(12) United States Patent
Kimura et al.

(10) Patent No.: US 10,070,046 B2
(45) Date of Patent: Sep. 4, 2018

(54) INFORMATION PROCESSING DEVICE, RECORDING MEDIUM, AND INFORMATION PROCESSING METHOD

(71) Applicant: SONY CORPORATION, Tokyo (JP)

(72) Inventors: Takaomi Kimura, Tokyo (JP); Hideyuki Matsunaga, Kanagawa (JP); Kosei Yamashita, Kanagawa (JP); Naofumi Fukasawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 74 days.

(21) Appl. No.: 14/917,201

(22) PCT Filed: Sep. 29, 2014

(86) PCT No.: PCT/JP2014/004979
§ 371 (c)(1),
(2) Date: Mar. 7, 2016

(87) PCT Pub. No.: WO2015/059874
PCT Pub. Date: Apr. 30, 2015

(65) Prior Publication Data
US 2016/0205317 A1 Jul. 14, 2016

(30) Foreign Application Priority Data

Oct. 24, 2013 (JP) .................................. 2013-221287

(51) Int. Cl.
*H04N 5/232* (2006.01)
*G09B 19/00* (2006.01)
(Continued)

(52) U.S. Cl.
CPC ..... *H04N 5/23219* (2013.01); *G06K 9/00342* (2013.01); *G09B 19/0038* (2013.01);
(Continued)

(58) Field of Classification Search
CPC .. A61B 5/1118; A61B 5/721; H04N 5/23219; H04N 21/42202; H04N 21/84;
(Continued)

(56) References Cited

U.S. PATENT DOCUMENTS

2002/0115046 A1 8/2002 McNitt et al.
2006/0291840 A1* 12/2006 Murata ................. H04N 5/772
396/50

(Continued)

FOREIGN PATENT DOCUMENTS

| EP | 2 781 240 A1 | 9/2014 |
| JP | 2010-273280 A | 12/2010 |
| WO | WO 02/066118 A1 | 8/2002 |

OTHER PUBLICATIONS

International Search Report dated Feb. 12, 2015 in PCT/JP2014/004979 filed on Sep. 29, 2014.

*Primary Examiner* — Ahmed A Berhan
(74) *Attorney, Agent, or Firm* — Oblon, McClelland, Maier & Neustadt, L.L.P.

(57) ABSTRACT

A non-transitory computer readable storage device includes a storage medium having a downloaded application stored therein. The downloaded application has instructions that when executed by processing circuitry configure the processing circuitry to receive sensor data from a sensor. The sensor is attached to a person or attached to an item used by the person. The processing circuitry also analyzes a motion pattern in the sensor data to identify a predetermined event in the motion pattern, the predetermined event captured in an image or series of images by an image capture device.

19 Claims, 17 Drawing Sheets

(51) Int. Cl.
  *G06K 9/00* (2006.01)
  *G06F 3/01* (2006.01)
  *G06F 3/0488* (2013.01)
  *A61B 5/11* (2006.01)
  *H04N 21/84* (2011.01)
  *H04N 21/845* (2011.01)

(52) U.S. Cl.
  CPC ............ *H04N 5/23245* (2013.01); *A61B 5/11* (2013.01); *A61B 2503/10* (2013.01); *A61B 2562/0219* (2013.01); *G06F 3/017* (2013.01); *G06F 3/0488* (2013.01); *H04N 21/84* (2013.01); *H04N 21/8456* (2013.01)

(58) Field of Classification Search
  CPC ........... H04N 5/23245; H04N 5/23293; H04N 21/8456; G06K 9/00342; G09B 19/0038
  See application file for complete search history.

(56) References Cited

U.S. PATENT DOCUMENTS

| | | | |
|---|---|---|---|
| 2007/0143130 A1 | 6/2007 | Hearn | |
| 2012/0188083 A1* | 7/2012 | Miller, II | A42B 3/046 340/573.1 |
| 2013/0130843 A1* | 5/2013 | Burroughs | A63B 71/0686 473/415 |
| 2014/0286621 A1 | 9/2014 | Matsunaga et al. | |

* cited by examiner

[Fig. 1]
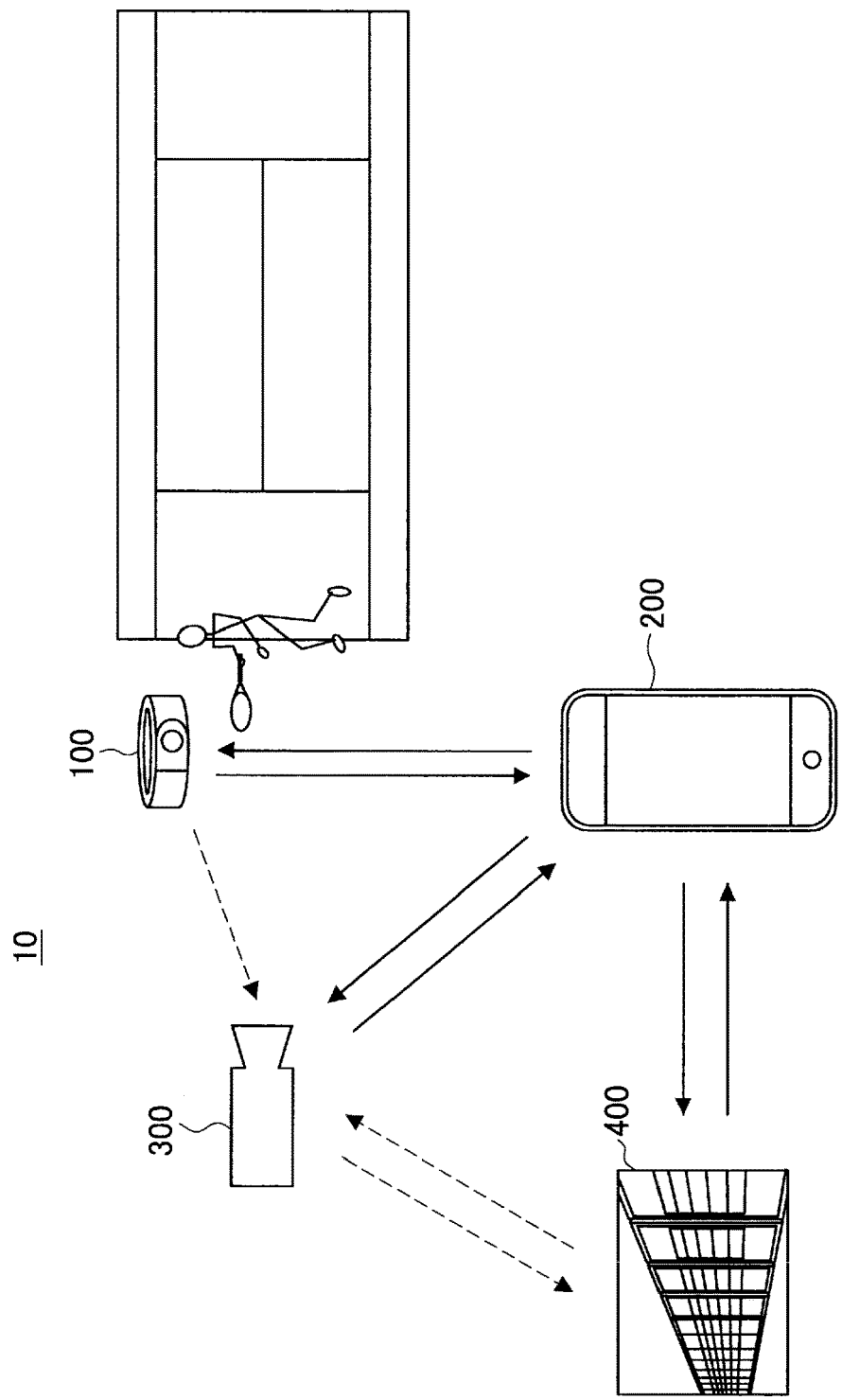

[Fig. 2]
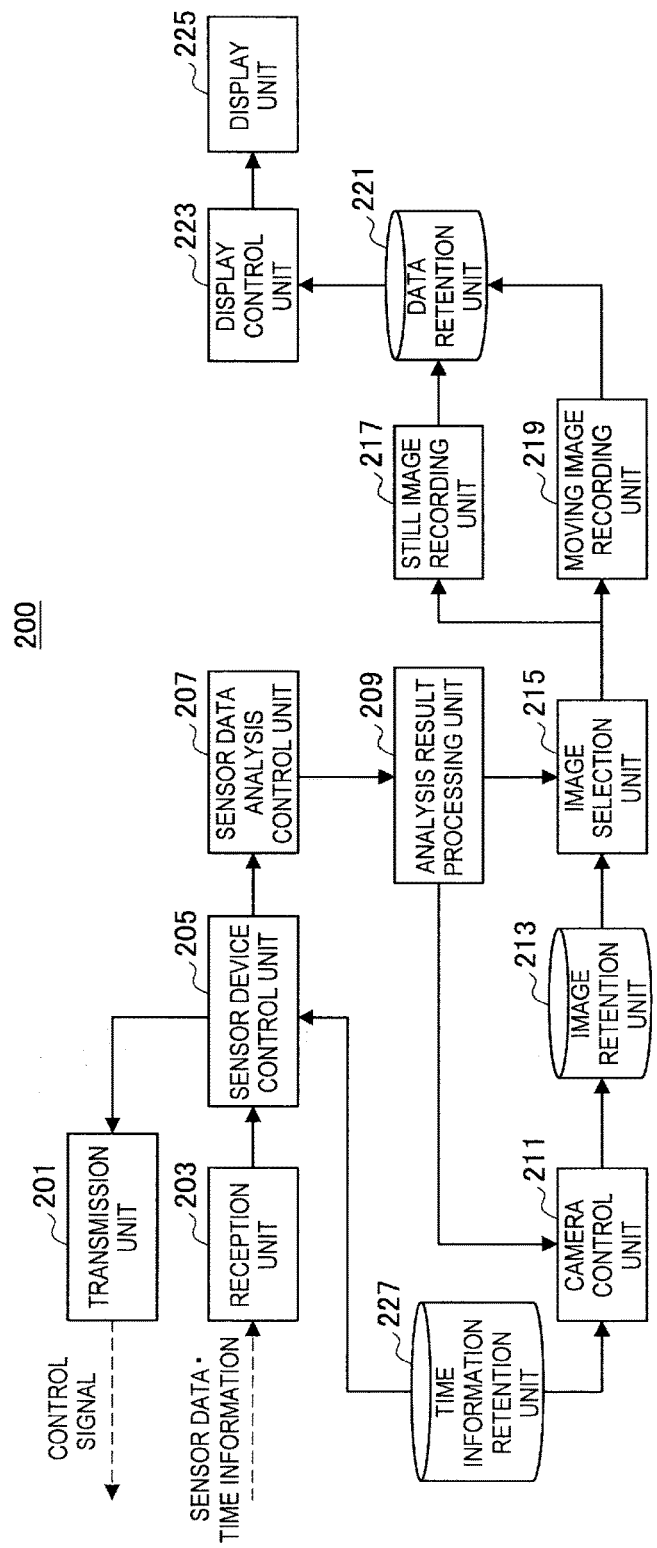

[Fig. 3]
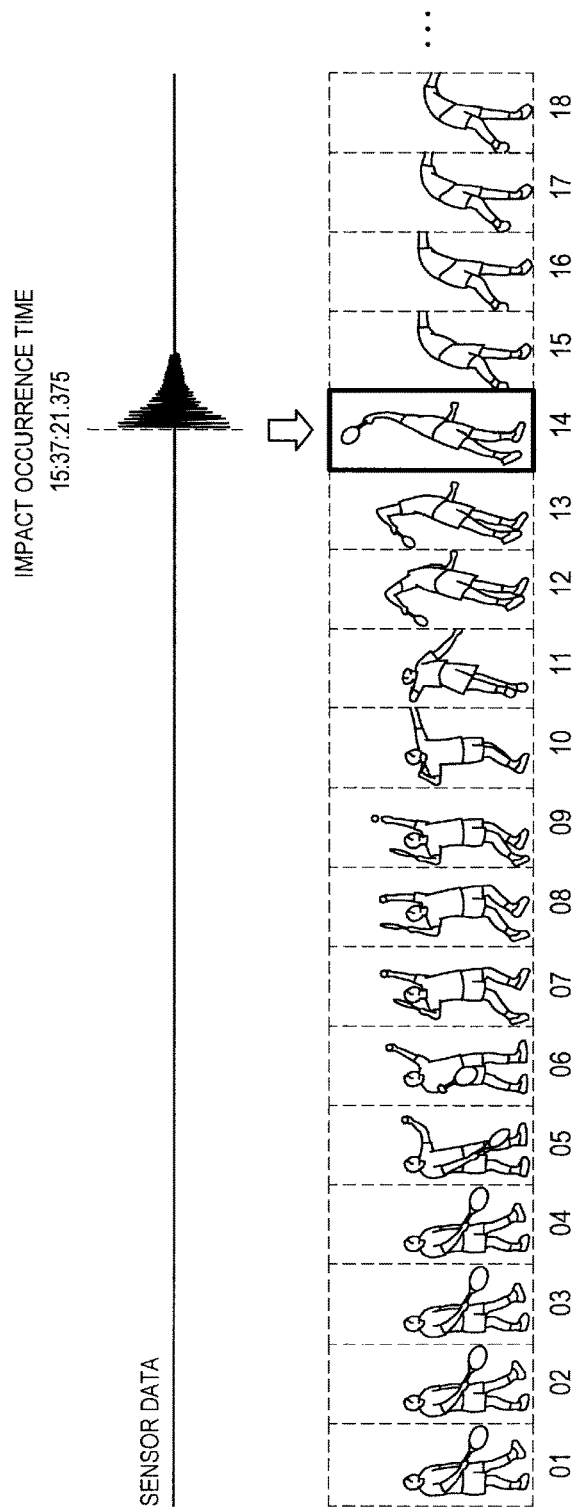

[Fig. 4]
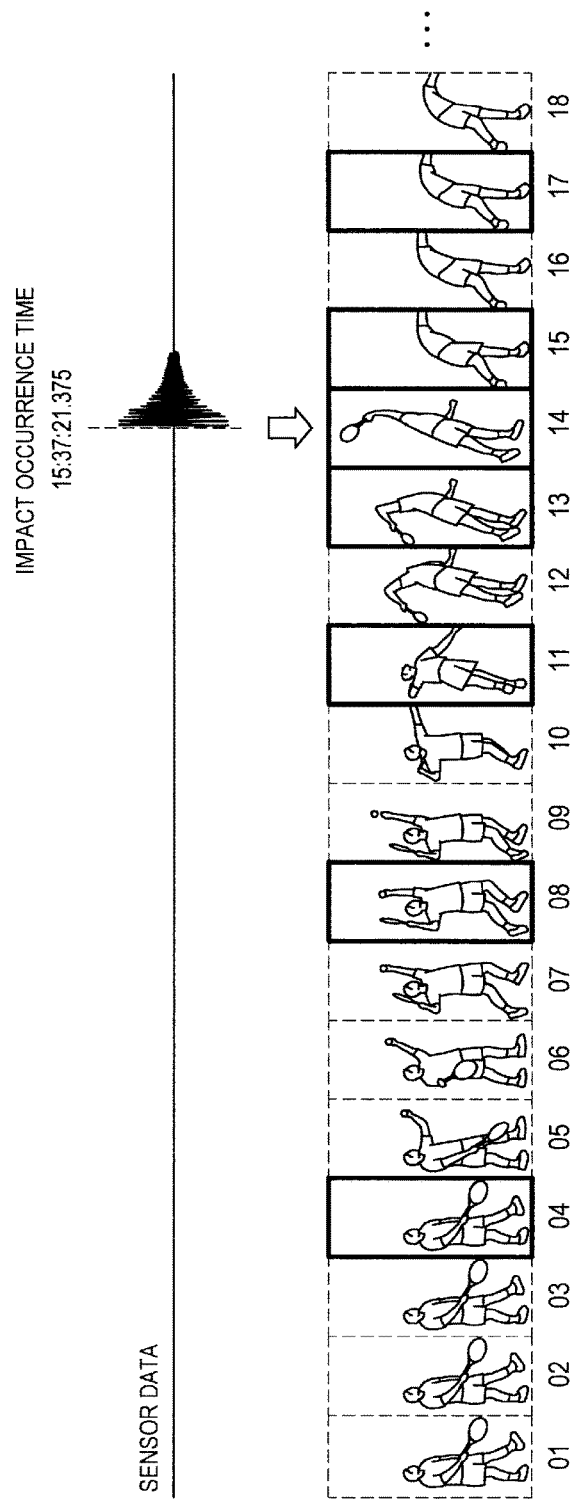

[Fig. 5]
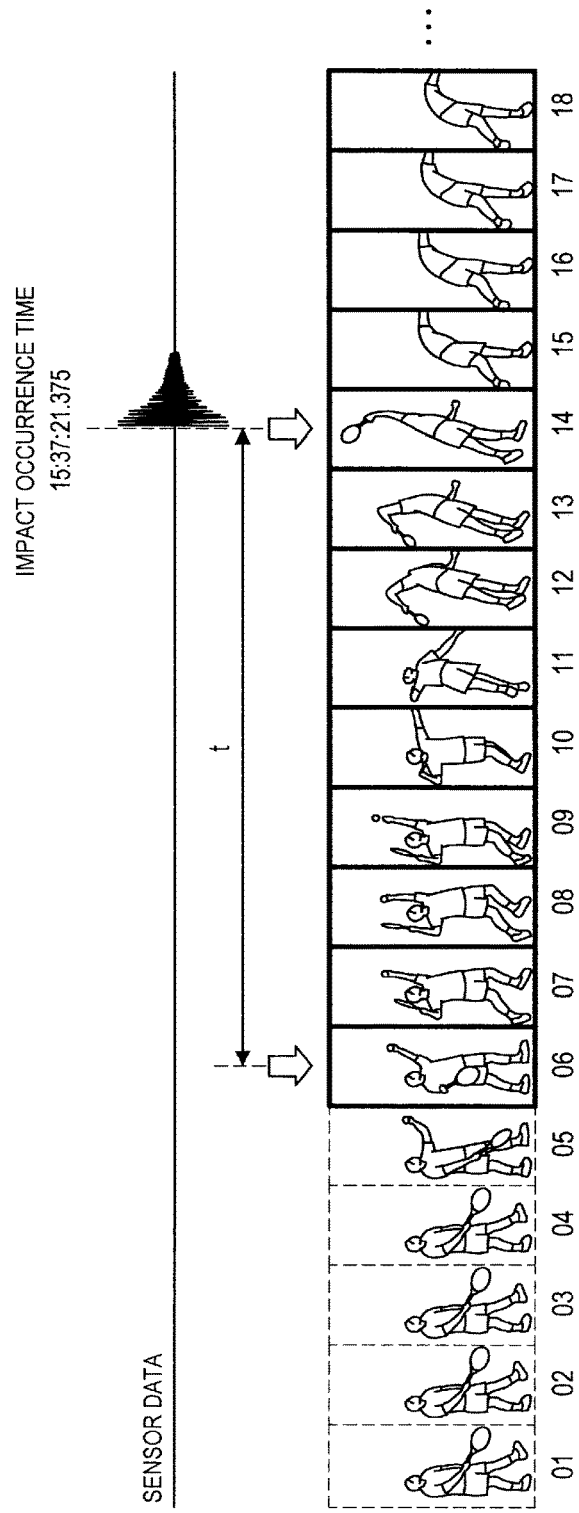

[Fig. 6]
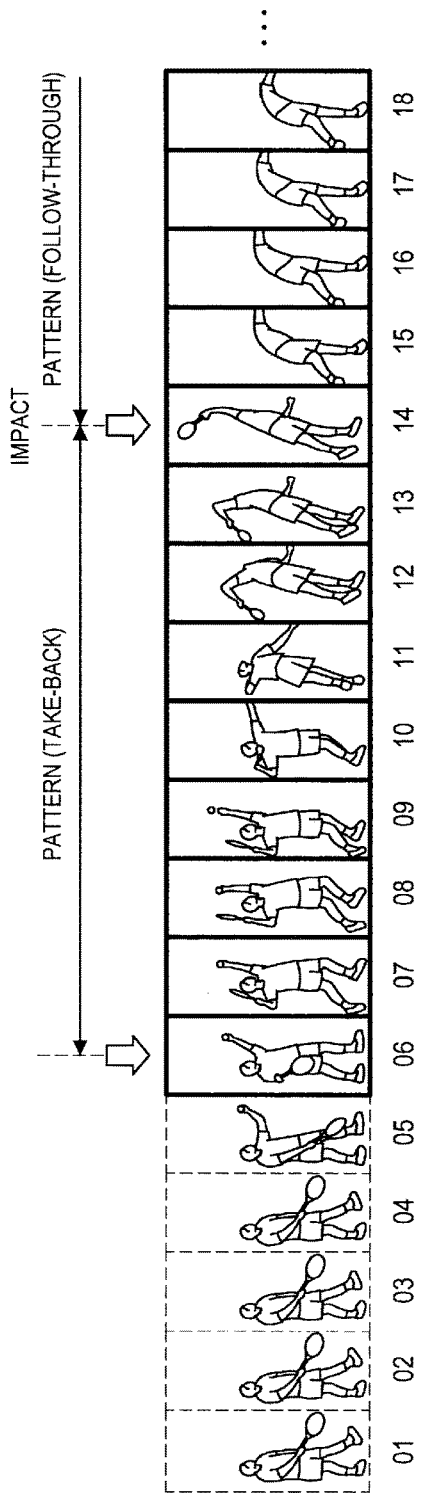

[Fig. 7]
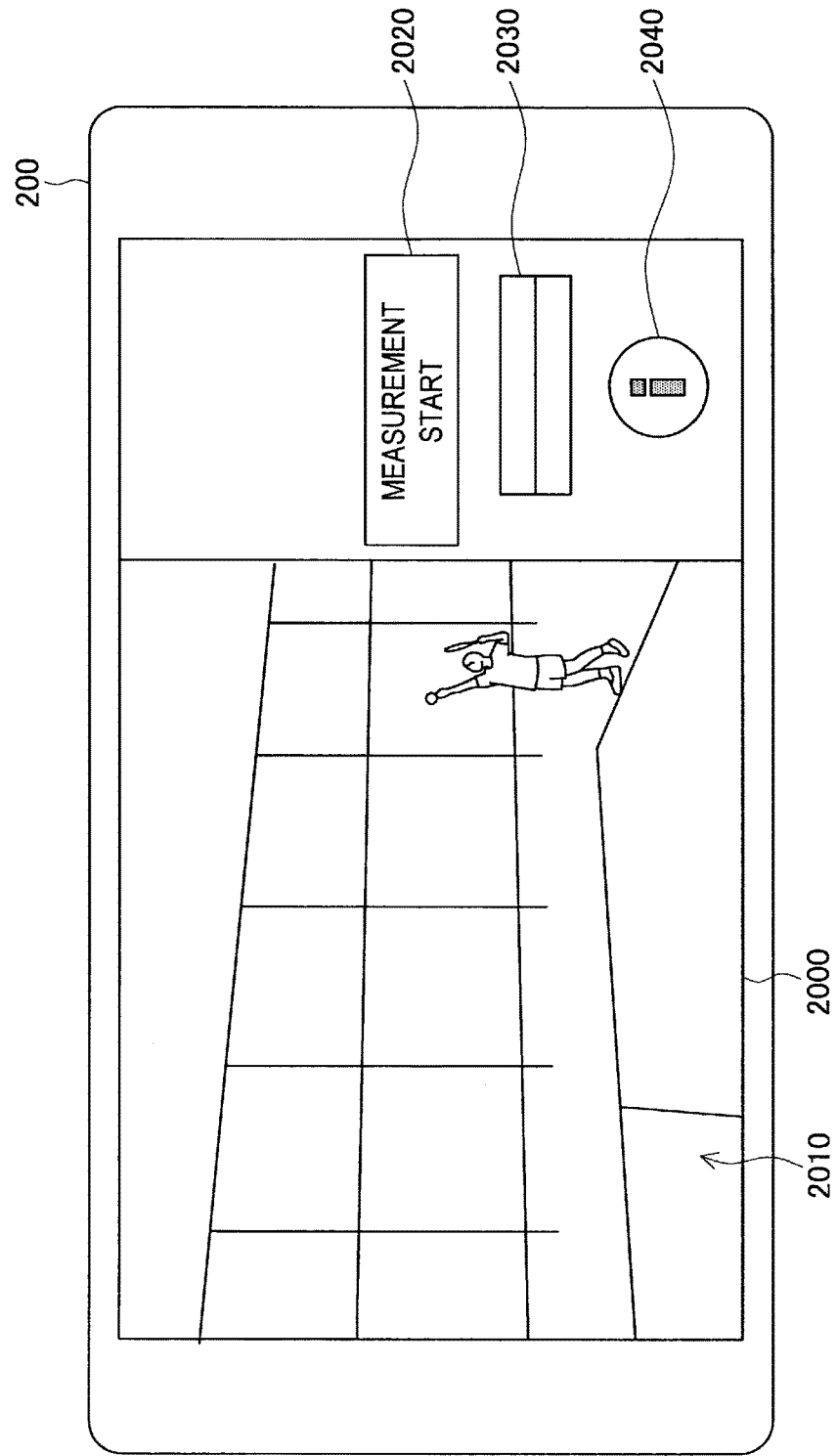

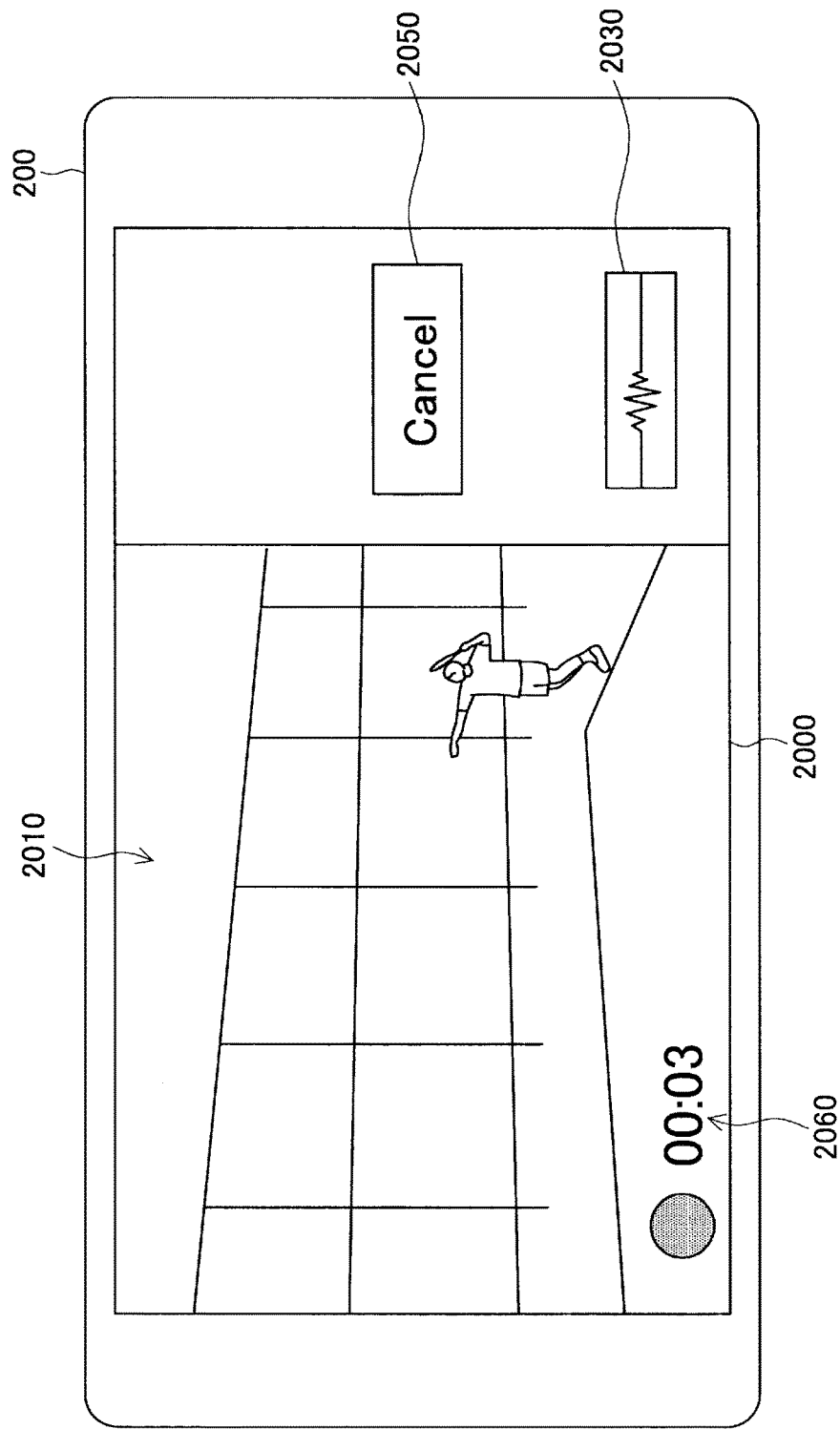
[Fig. 8]

[Fig. 9]
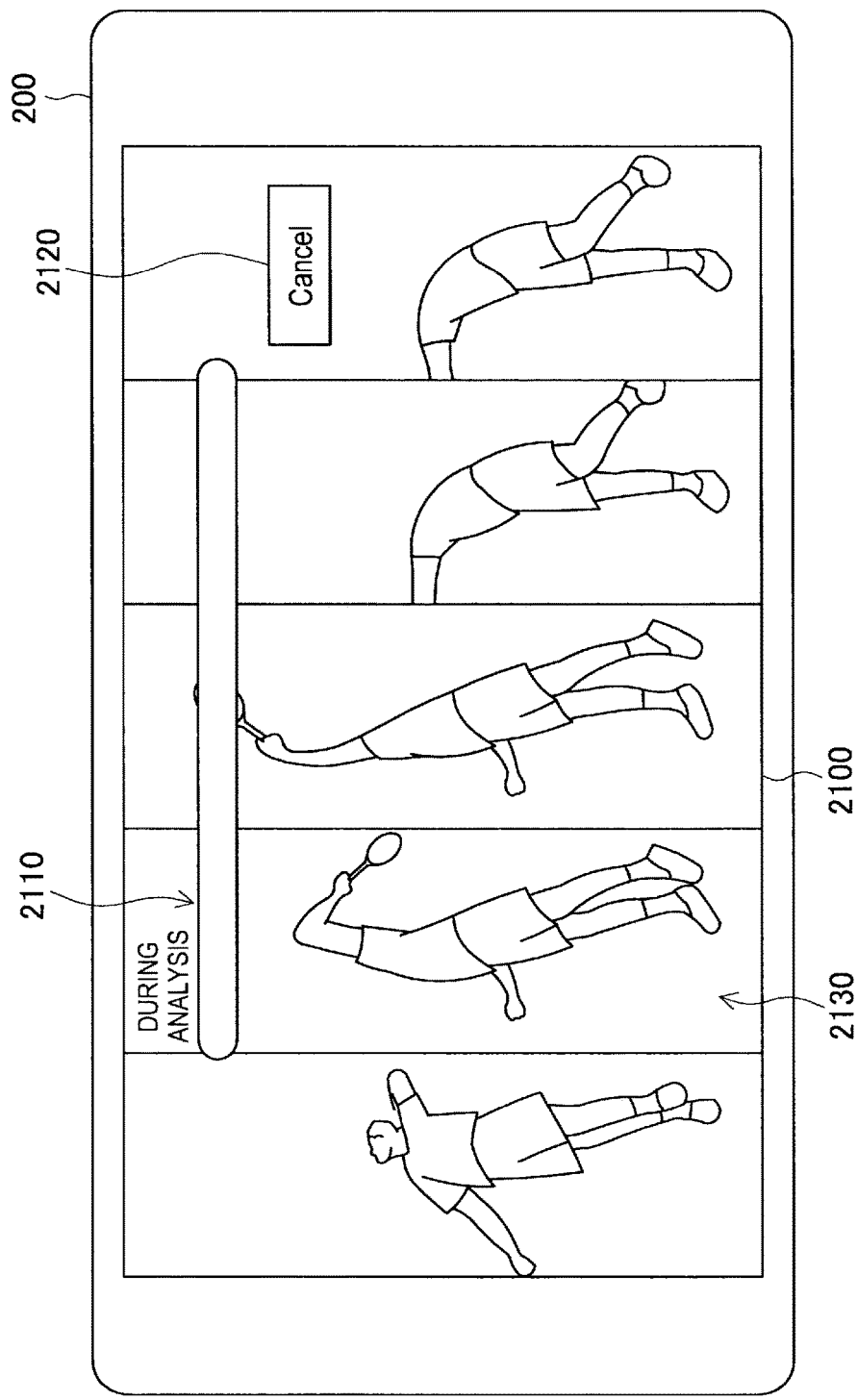

[Fig. 10]
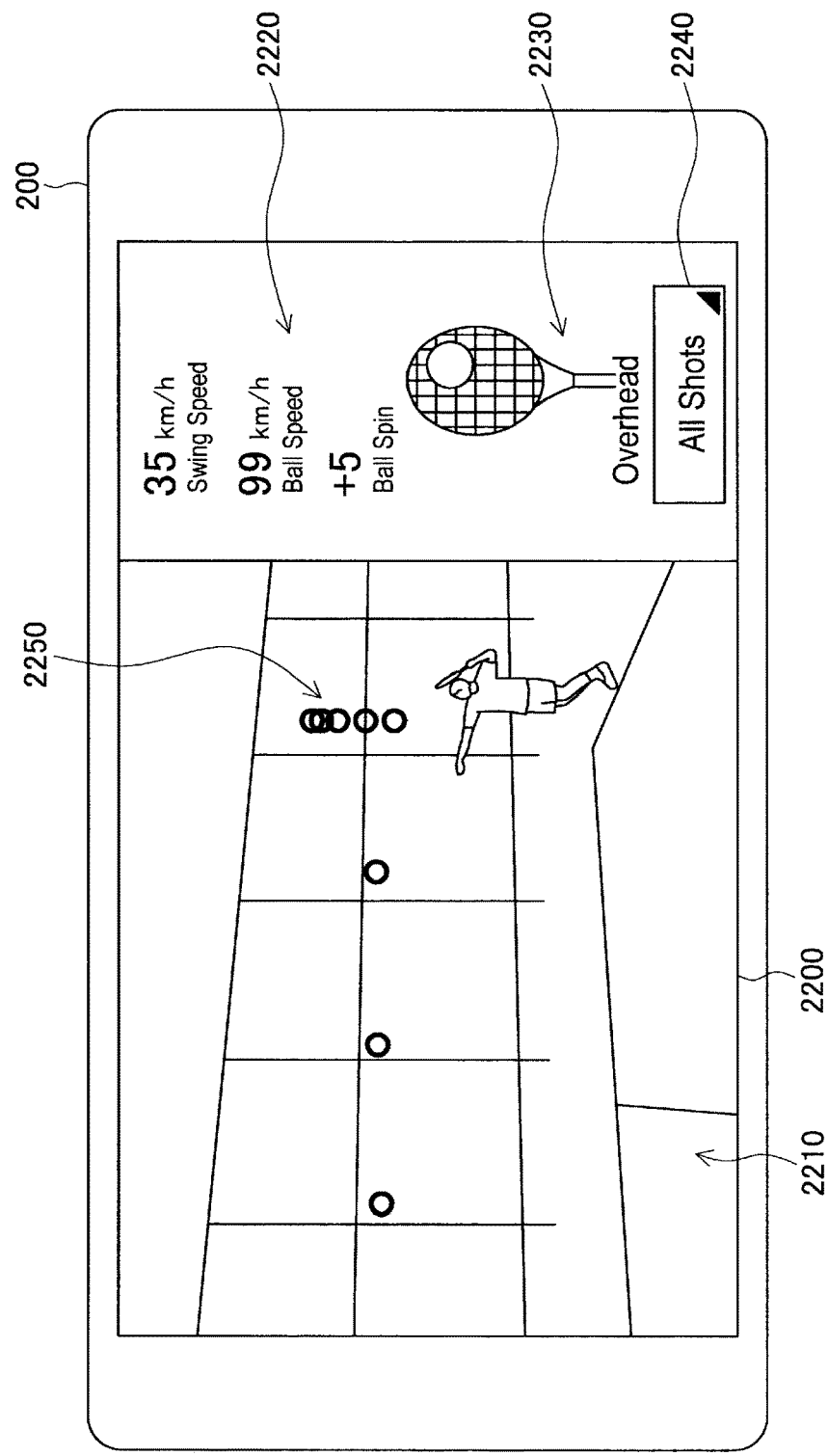

[Fig. 11]
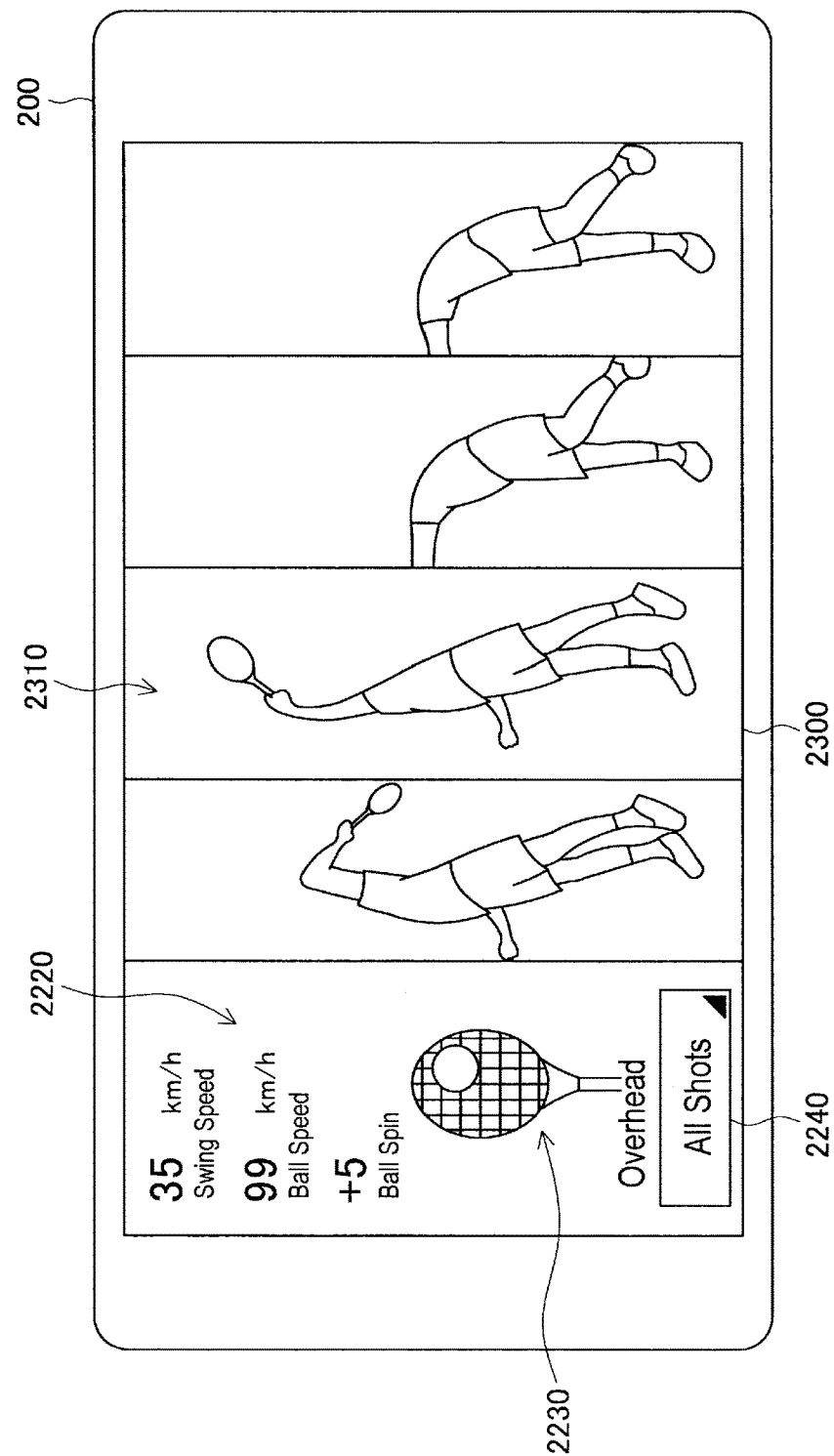

[Fig. 12]
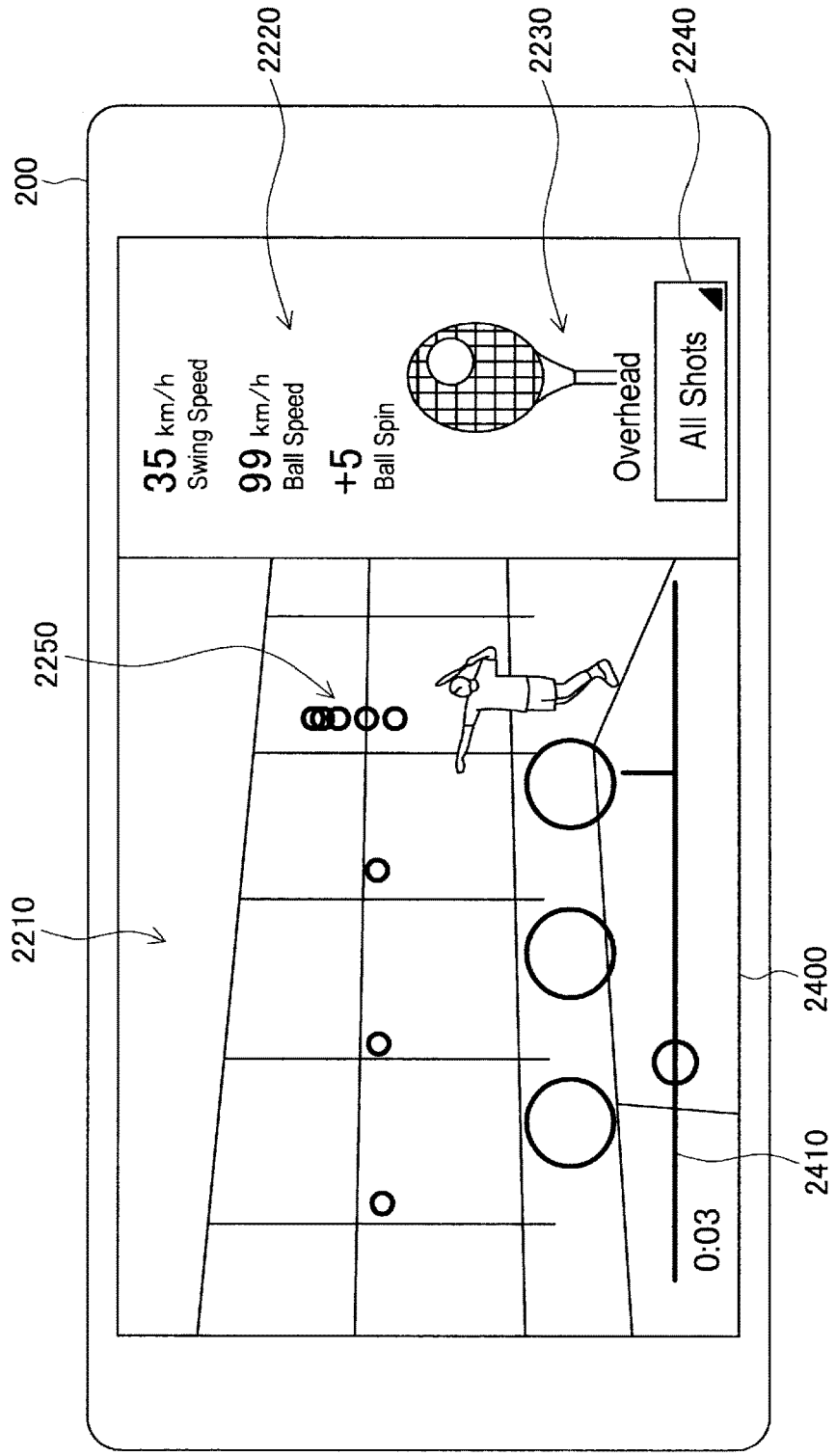

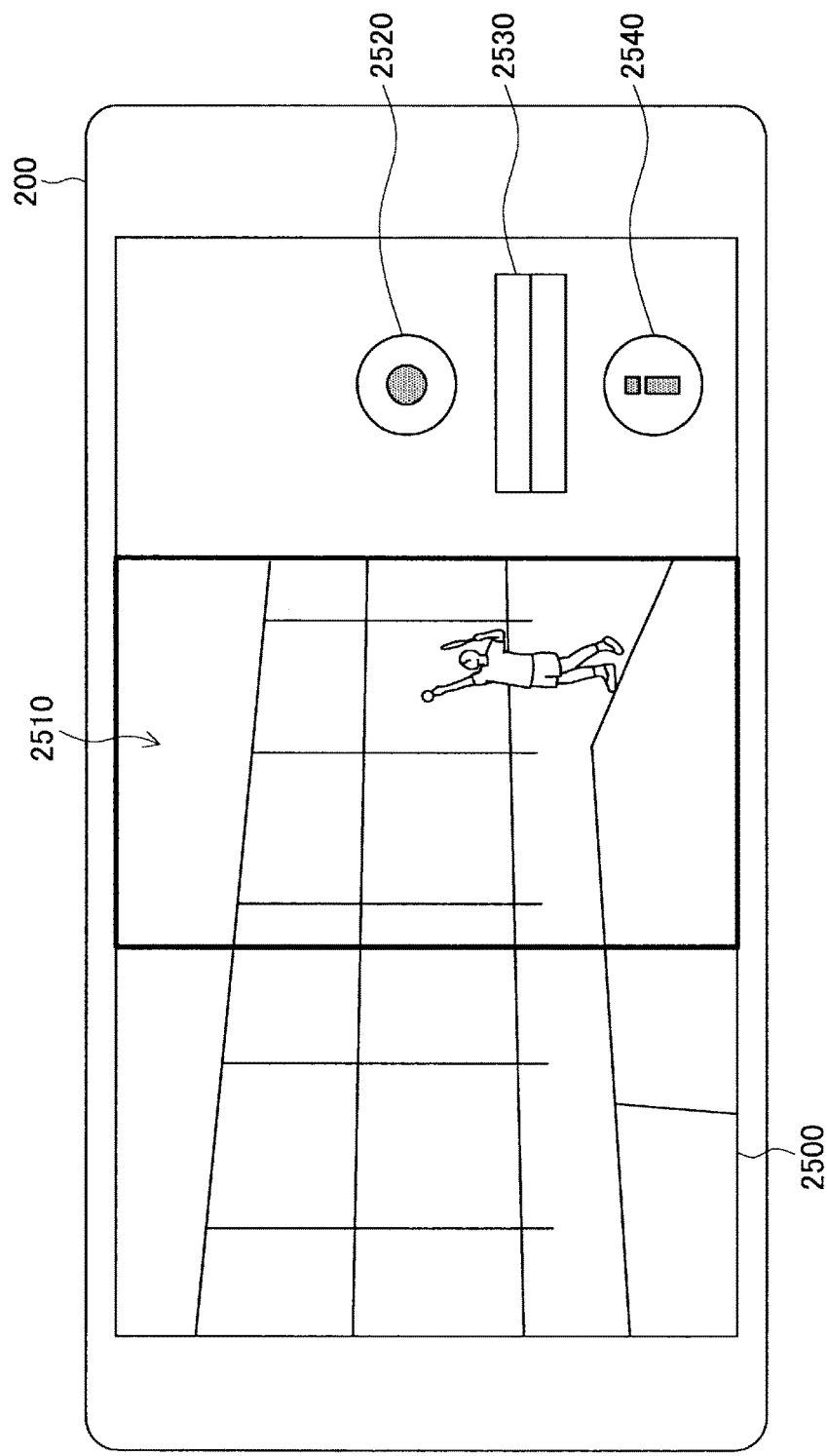
[Fig. 13]

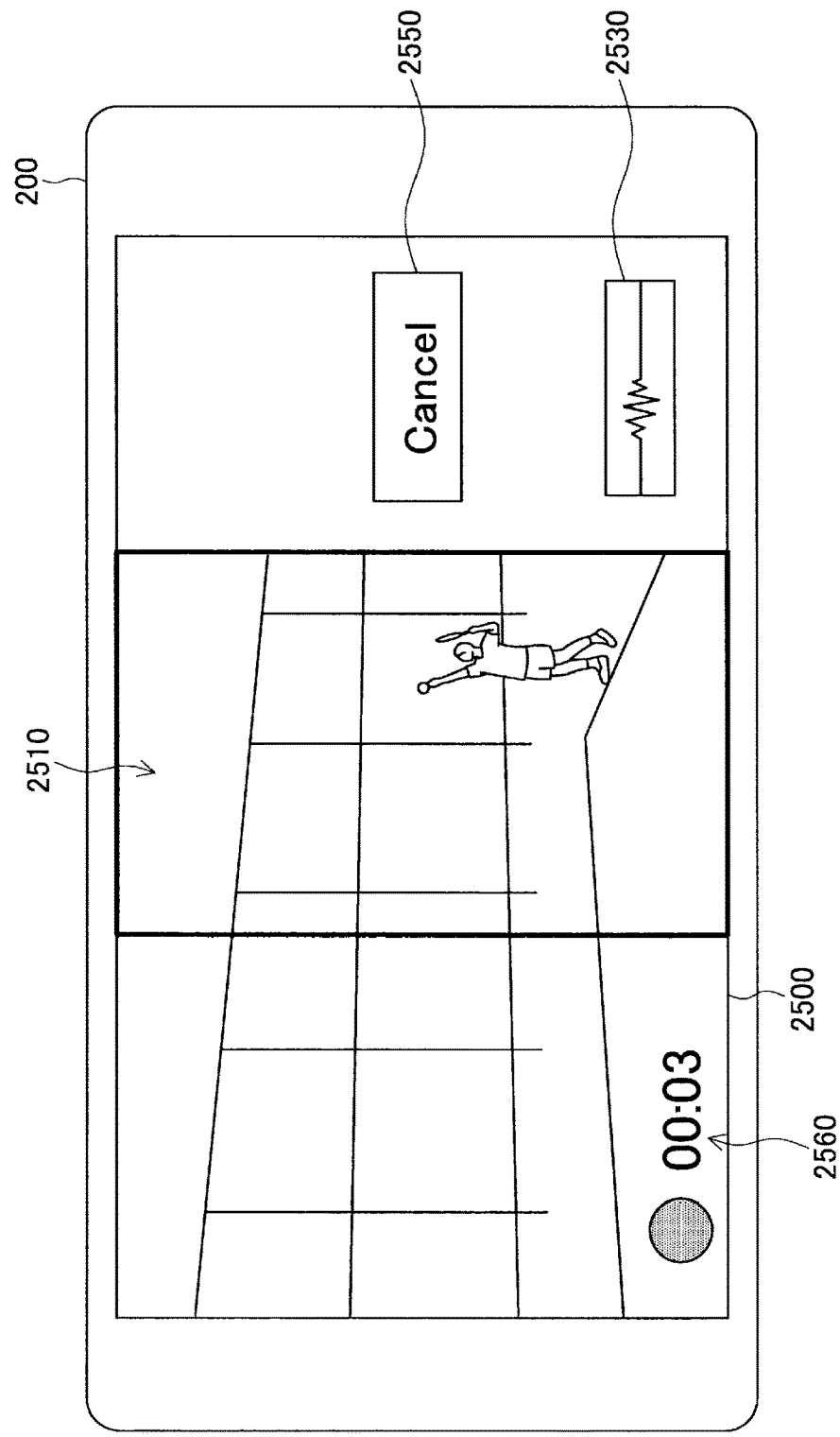
[Fig. 14]

[Fig. 15]
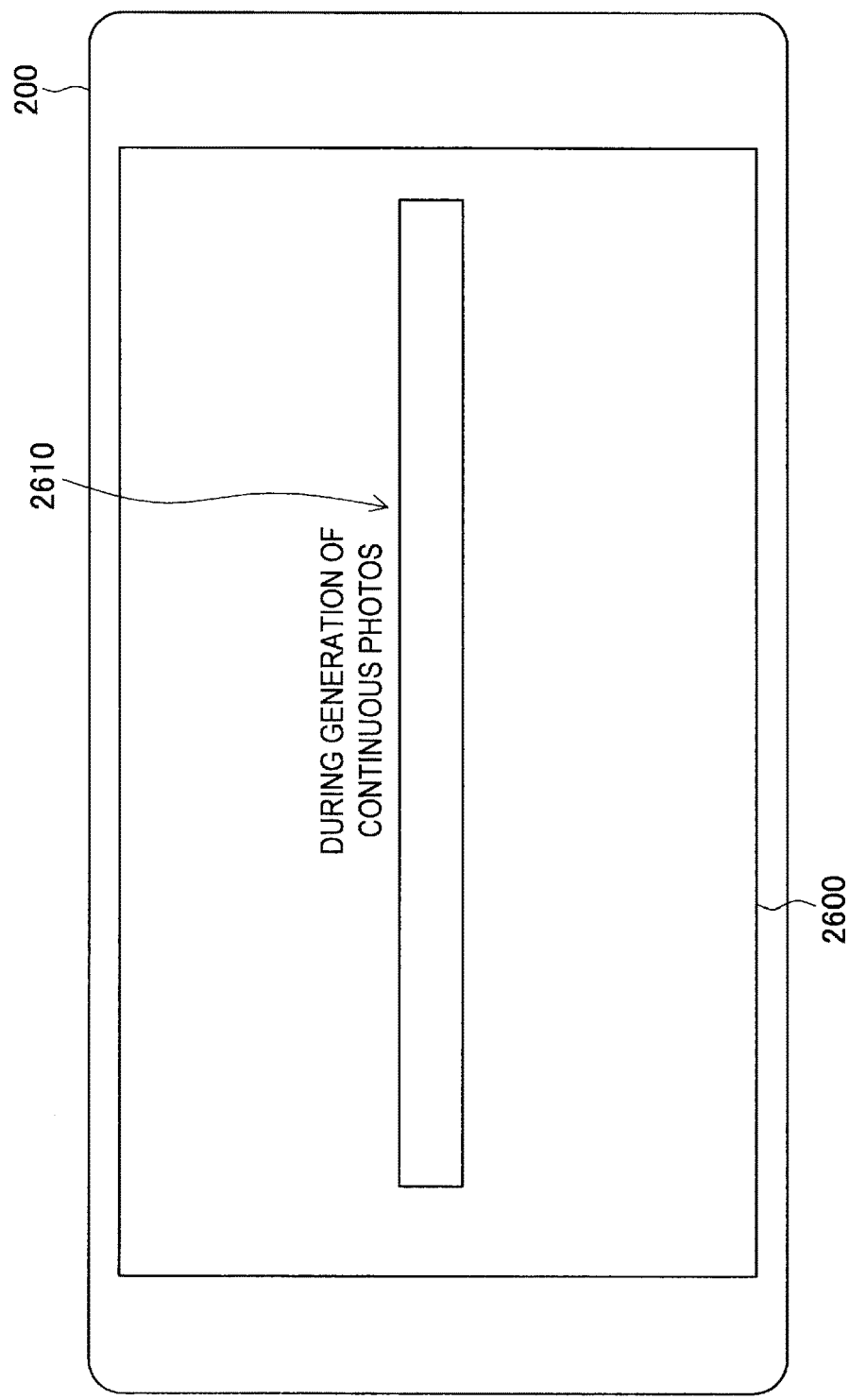

[Fig. 16]
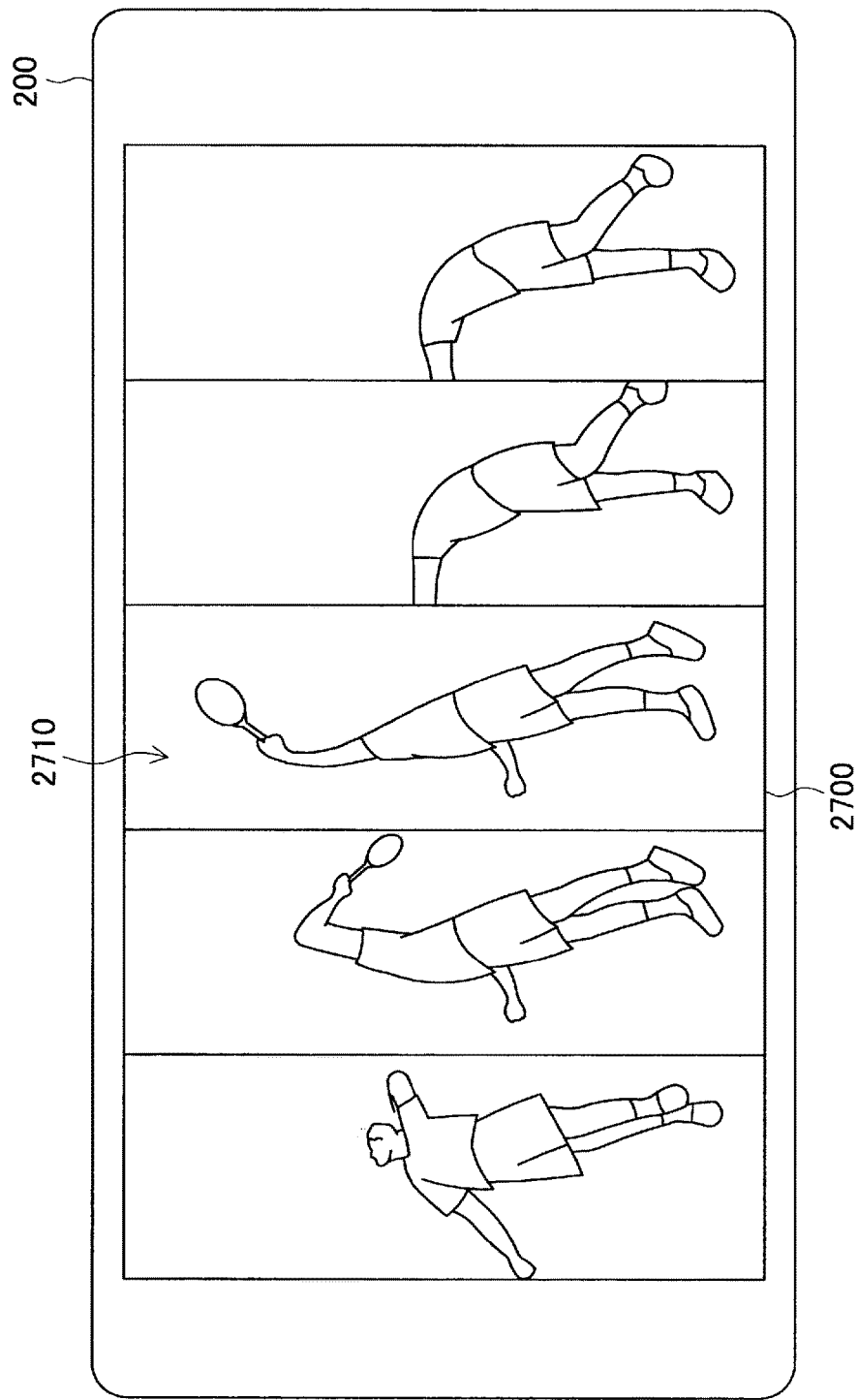

[Fig. 17]
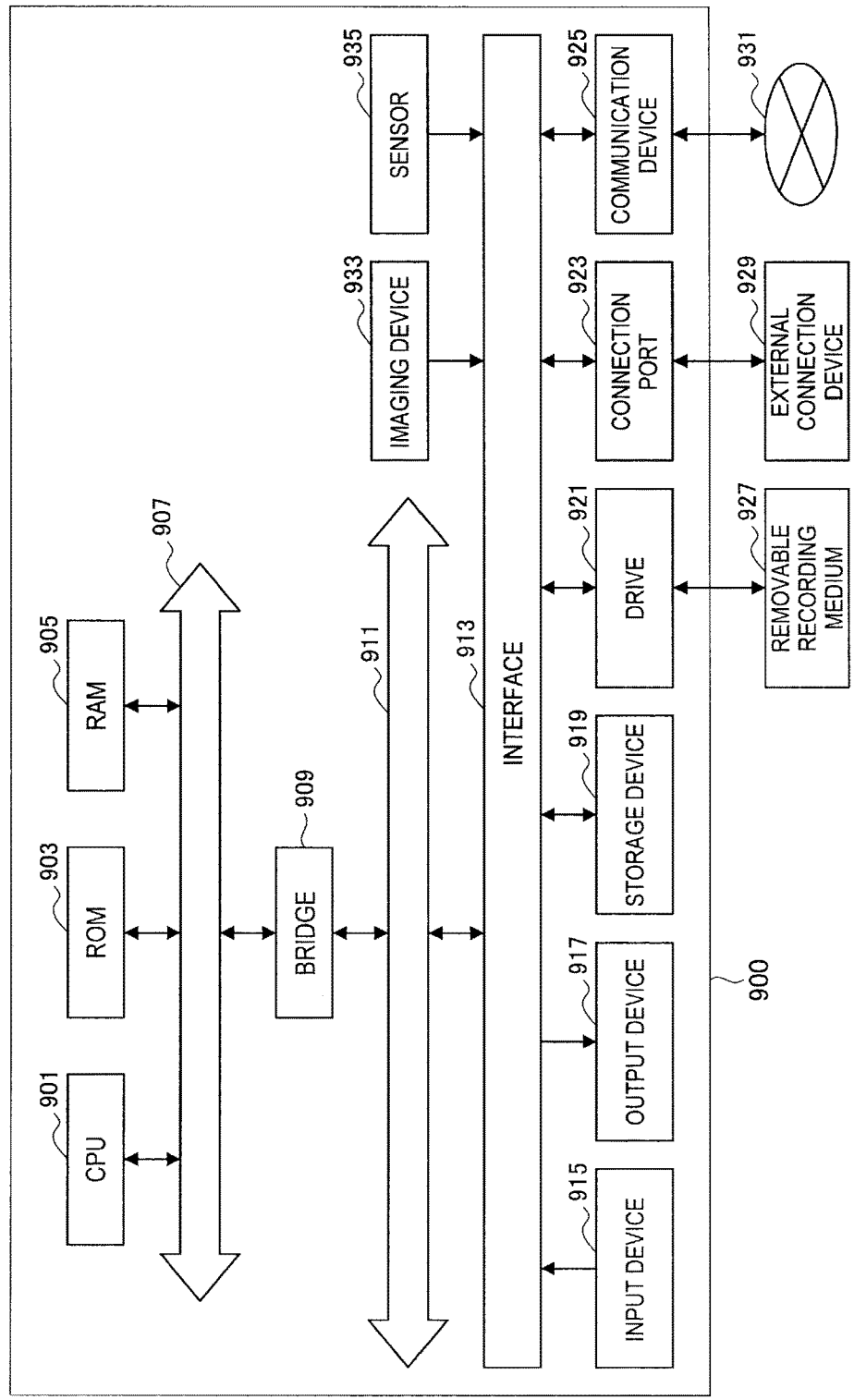

INFORMATION PROCESSING DEVICE, RECORDING MEDIUM, AND INFORMATION PROCESSING METHOD

CROSS REFERENCE TO RELATED APPLICATIONS

This application claims the benefit of Japanese Priority Patent Application JP 2013-221287 filed Oct. 24, 2013, the entire contents of which are incorporated herein by reference.

TECHNICAL FIELD

The present disclosure relates to an information processing device, a recording medium, and an information processing method.

BACKGROUND ART

Cameras or devices equipped with cameras have become widespread, and thus images (still images or moving images) of users are now generally photographed in various scenes. In such cases, many images are expected to capture so-called important moments. For example, when images are photographed during sports play, users may want to record many important moments, such as ball impact moments, jumping moments, landing moments, and technique decision moments, as images. As a technology for recording such important moments as images, for example, PTL 1 discloses a technology for detecting expressions or actions (gestures) of subjects, which are release triggers, from through images and dynamically performing the photographing when the expressions or the actions are detected.

CITATION LIST

Patent Literature

PTL 1: JP 2010-273280A

SUMMARY

Technical Problem

However, for example, sports plays contain a variety of continuous motions, and thus it is not easy to characterize important moments from through images. Further, unlike expressions or the like, duration times of the important moments are very short in many cases. In this case, it is difficult to correctly detect the important moments by applying, for example, the technology disclosed in PTL 1 and detecting expressions or actions of subjects from through images.

It is desirable to provide a novel and improved information processing device, a novel and improved recording medium, and a novel and improved information processing method capable of accurately specifying an important moment among continuous motions of a subject and extracting the important motion as an image.

Solution to Problem

The following are examples of solutions described herein to the issues with conventional systems and methods.

According to a non-transitory computer readable storage device embodiment, a storage medium has an application stored therein. The application has instructions that when executed by processing circuitry configure the processing circuitry to receive sensor data from a sensor, the sensor being attached to a person or attached to an item used by the person; and analyze a motion pattern in the sensor data to identify a predetermined event in the motion pattern, the predetermined event captured in an image or series of images by an image capture device.

An information processing system comprising:

circuitry, the circuitry configured by computer readable instructions to receive sensor data collected by a sensor attached to a person or attached to an item used by the person; and analyze a motion pattern in the sensor data to identify a predetermined event in the motion pattern, the predetermined event captured in an image or series of images by an image capture device.

Advantageous Effects of Invention

According to an embodiment of the present disclosure described above, it is possible to accurately specify an important moment among continuous motions of a subject and extract the important moment as an image.

The foregoing advantageous effects are not necessarily restrictive, but any advantageous effect desired to be obtained in the present specification or other advantageous effects understood from the present specification may be obtained along with the foregoing advantageous effects or instead of the foregoing advantageous effects.

BRIEF DESCRIPTION OF DRAWINGS

FIG. 1 is a diagram illustrating an overall configuration of a system according to an embodiment of the present disclosure.

FIG. 2 is a diagram illustrating an overall functional configuration of a smartphone according to the embodiment of the present disclosure.

FIG. 3 is a diagram for describing an example in which a single still image is selected according to the embodiment of the present disclosure.

FIG. 4 is a diagram for describing an example in which continuous photos are selected according to the embodiment of the present disclosure.

FIG. 5 is a diagram for describing an example in which a section of a moving image is set according to the embodiment of the present disclosure.

FIG. 6 is a diagram for describing an example in which images are selected based on a continuous motion pattern according to the embodiment of the present disclosure.

FIG. 7 is a diagram illustrating a start screen of a shot diagnosis application.

FIG. 8 is a diagram illustrating a screen during measurement in the shot diagnosis application.

FIG. 9 is a diagram illustrating a screen during analysis in the shot diagnosis application.

FIG. 10 is a diagram illustrating a result screen of the shot diagnosis application.

FIG. 11 is a diagram illustrating a continuous photo screen of the shot diagnosis application.

FIG. 12 is a diagram illustrating a reproduction control screen of the shot diagnosis application.

FIG. 13 is a diagram illustrating a start screen of a continuous photo generation application.

FIG. 14 is a diagram illustrating a screen during photographing in the continuous photo generation application.

FIG. 15 is a diagram illustrating a screen during generation in the continuous photo generation application.

FIG. 16 is a diagram illustrating a generation result screen of the continuous photo generation application.

FIG. 17 is a block diagram illustrating an example of a hardware configuration of an information processing device according to an embodiment of the present disclosure.

DESCRIPTION OF EMBODIMENTS

Hereinafter, preferred embodiments of the present disclosure will be described in detail with reference to the appended drawings. Throughout the present specification and the drawings, the same reference numerals are given to constituent elements having substantially the same configurations and repeated description will be omitted.

The description will be made in the following order.
1. System configuration
2. Functional configuration
3. Examples of image selection
3-1. Example in which single still image is selected
3-2. Example in which continuous photos are selected
3-3. Example in which section of moving image is set
3-4. Example in which continuous motion pattern is detected
4. Examples of applications
4-1. Shot diagnosis application
4-2. Continuous photo generation application
5. Hardware configuration
6. Supplement (1. System Configuration)

FIG. 1 is a diagram illustrating an overall configuration of a system according to an embodiment of the present disclosure. Referring to FIG. 1, a system 10 includes a sensor device 100, a smartphone 200, a camera 300, and a server 400. Although a smartphone 200 is shown in this embodiment, a wearable computer may be used as well, such as smartglasses (such as SONY SMARTEYEGLASS), smartwatch (such as SONY SMARTWATCH 2), action camera (such as SONY POV HD), activity tracker (such as SONY SMARTBAND), etc.

The sensor device 100 is a sensor mounted on a user or an object coming into contact with the user. In this context, a "user" may also be an animal or a machine. In the illustrated example, the user is playing a sport (tennis). In this example, for example, the sensor device 100 can be inserted into a grip portion of a tennis racket gripped by the user or can be wound around a shaft portion. The tennis racket is an object coming into contact with the user. Alternatively, the sensor device 100 may have a bracelet shape and may be mounted on a wrist of the user. As another example, the sensor device 100 may be mounted on, for example, another part of the body of the user, such as an arm or an ankle. When the sensor device 100 is mounted on an object such as a tennis racket, the sensor device 100 may be an object, e.g., a batting tool such as a racket or a sports tool such as clothing, shoes, or a wristband. In this case, the sensor device 100 may be wound around the object, sewed on the object, attached to the object, or built in the object in advance to be mounted.

For example, the sensor device 100 includes a sensor that acquires sensor data indicating a behavior of the user, a processing circuit that processes the sensor data, and a communication device that communicates with the smartphone 200. For example, the sensor acquires sensor data regarding an acceleration, an angular velocity, vibration, a temperature, a time, a position (for example, a position on the surface of the earth indicated by a latitude and a longitude or a relative position with respect to a court or the like). The processing circuit preprocesses the sensor data, as necessary. The communication device performs, for example, wireless communication such as Bluetooth (registered trademark) with the smartphone 200. Through the wireless communication, for example, the sensor data (including the data preprocessed by the processing circuit) is transmitted from the sensor device 100 to the smartphone 200. Through the wireless communication, a control signal may be transmitted from the smartphone 200 to the sensor device 100. In this case, the sensor and/or the processing circuit operate according to the control signal received by the communication device.

The smartphone 200 is an example of an information processing device used by the user. In the illustrated example, the smartphone 200 is put near the user who is playing the sport (tennis). For example, the user uses the smartphone 200 during the play to use a play support application to be described below. The smartphone 200 can perform various processes through a linkage operation with the sensor device 100 or the camera 300 while the user does not use the smartphone 200, that is, the user is playing the sport. For example, the smartphone 200 may control recording of images photographed by the camera 300 based on the sensor data received from the sensor device 100. The smartphone 200 may control a photographing operation of the camera 300 by transmitting a control signal generated based on the sensor data to the camera 300. The smartphone 200 may also transmit a control signal to the sensor device 100 in the same way. The smartphone 200 may upload the sensor data received from the sensor device 100 or images photographed by the camera 300 to the server 400. The smartphone 200 may make a request for some or all of the processes related to the linkage operation with the sensor device 100 or the camera 300 to the server 400.

For example, the smartphone 200 includes a processor that performs a process on the sensor data or images, a memory or a storage that stores the sensor data, the images, and various kinds of intermediate data, a display that displays a screen of a play support application or the like for the user, a manipulation unit such as touch panel that acquires a manipulation input of the user, and a communication device that performs communication with the sensor device 100, the camera 300, and the server 400. For example, the communication device can include a communication device that performs wireless communication such as Bluetooth (registered trademark) with the sensor device 100 and the camera 300 and a communication device that performs network communication with the server 400. Functions realized by this hardware configuration will be described below. An example of a more specific hardware configuration of the information processing device capable of realizing the smartphone 200 will also be described below.

The camera 300 is an example of an imaging device capable of photographing images containing a user as a subject. The photographed images may be still images or moving images. In the illustrated example, the camera 300 is located at a position at which the user who is playing the sport (tennis) can be photographed, e.g., a side or the like of the court. In the embodiment, the camera 300 performs a linkage operation with the smartphone 200. For example, the camera 300 may transmit some or all of the photographed images to the smartphone 200. For example, the camera 300 may perform photographing according to a control signal received from the smartphone 200. A more specific example of the linkage operation between the camera 300 and the smartphone 200 will be described below.

For example, the camera 300 includes an optical system such as an imaging element and a lens, a control unit that controls the imaging element and the optical system, a memory or a storage that temporarily or permanently stores photographed images, a processor that processes the photographed images, and a communication device that performs communication with the smartphone 200. For example, the communication device performs wireless communication such as Bluetooth (registered trademark) with the smartphone 200. Through the wireless communication, for example, the photographed images are transmitted from the camera 300 to the smartphone 200. Through the wireless communication, a control signal may be transmitted from the smartphone 200 to the camera 300. In this case, the control unit and/or the processor operates according to the control signal received by the communication device. The camera 300 may also be realized by the hardware configuration of the information processing device to be described below.

The server 400 communicates with the smartphone 200 via a network to receive uploading of the sensor data or images or performs a process in response to a request from the smartphone 200. For example, for a single user, the system 10 can be completed without including the server 400. In contrast, when there are a plurality of users, data or images can be uploaded to the server 400, so that the images can be shared between the users or a pattern of the sensor data can be learned based on the data of the plurality of users. When the server 400 performs a process in response to a request from the smartphone 200, a processing load of the smartphone 200 can be reduced. Whether the processing software is hosted in the server 400 or smartphone 200 (or distributed therebetween) the software may be downloadable as a programing application that configures the processor(s) running in the server 400 and/or smartphone 200.

For example, the server 400 is realized by one or more server devices each including a processor that performs a process on the sensor data or images and other processes requested by the smartphones 200, a memory or a storage that stores the uploaded sensor data or images and various kinds of intermediate data, and a communication device that performs communication with the smartphones 200. The communication device performs network communication with the smartphones 200. As described above, through the network communication, for example, the sensor data or the images are uploaded from the smartphones 200 to the server 400. Through the network communication, data requested by the smartphones 200 from the server 400 or results of the processes performed by the server 400 in the request of the smartphones 200 may be transmitted from the server 400 to the smartphones 200. A more specific hardware configuration of the information processing device capable of realizing the server device configuring the server 400 will be described below.

The above-described configuration of the system 10 is merely an example and various other configurations of the system can be realized. For example, the camera 300 may be built in the smartphone 200. In this case, exchange of data through wireless communication between the camera 300 and the smartphone 200 in the system 10 described above is substituted with exchange of data via an internal bus or the like of the smartphone 200. In this case, the smartphone 200 may be substituted with various terminal devices having a photographing function, a processing function, and a communication function, e.g., tablet terminals or game devices.

When the camera 300 is separated from the smartphone 200, the smartphone 200 can be substituted with various terminal devices having a processing function and a communication function, e.g., various personal computers.

As another example, some of the functions of the smartphone 200 described above may be realized by the camera 300. For example, the sensor device 100 may communicate with the camera 300 and the camera 300 may control the photographing based on the sensor data received from the sensor device 100. In this case, the camera 300 can serve as an information processing device according to an embodiment of the present disclosure. In this case, the system 10 may not include the smartphone 200. The camera 300 may communicate with the server 400 and upload images directly to the server 400. Likewise, the sensor device 100 may upload the sensor data directly to the server 400. In this case, the sensor device 100 may not directly communicate with the camera 300 and the camera 300 can be controlled by the server 400 based on the sensor data transmitted from the sensor device 100 to the server 400. In this case, the server 400 can be said to serve as an information processing device according to an embodiment of the present disclosure.

(2. Functional Configuration)

FIG. 2 is a diagram illustrating an overall functional configuration of a smartphone according to the embodiment of the present disclosure. Referring to FIG. 2, the smartphone 200 includes a transmission unit 201, a reception unit 203, a sensor device control unit 205, a sensor data analysis unit 207, an analysis result processing unit 209, a camera control unit 211, an image retention unit 213, an image selection unit 215, a still image recording unit 217, a moving image recording unit 219, a data retention unit 221, a display control unit 223, a display unit 225, and a time information retention unit 227 as a functional configuration. Hereinafter, the functional configuration will be further described.

The transmission unit 201 and the reception unit 203 are realized by a communication device. The transmission unit 201 transmits a control signal to the sensor device 100. The control signal may include, for example, a command to start/end detection of the sensor data and transmission of the sensor data to the smartphone 200. The control signal may include a command to adjust a time with which the sensor device 100 associates the sensor data. As will be described below, when a process is performed based on the sensor data acquired in the sensor device 100 and an image photographed by the camera 300, the smartphone 200 synchronizes the sensor data and the image with reference to a time. Accordingly, in the embodiment, the smartphone 200 can transmit a command to adjust a time to the devices so that a time associated with the sensor data in the sensor device 100 matches a time associated with the image in the camera 300. In another embodiment, when the sensor data and the image can be synchronized regardless of times associated in the devices, the control signal may not include the command to adjust a time. The reception unit 203 receives the sensor data and time information corresponding to the sensor data from the sensor device 100.

The sensor device control unit 205 is realized by a processor. The sensor device control unit 205 controls the sensor device 100 via the transmission unit 201 and the reception unit 203 and acquires the sensor data supplied by the sensor device 100 and time information corresponding to the sensor data. The sensor device control unit 205 supplies the received sensor data and time information to the sensor data analysis unit 207. The sensor device control unit 205 acquires a time included in a time adjustment command to be transmitted to the sensor device 100 via the transmission unit 201 from the time information retention unit 227.

The sensor data analysis unit 207 is realized by a processor. The sensor data analysis unit 207 analyzes the sensor data supplied from the sensor device control unit 205 and supplies the analysis result to the analysis result processing unit 209. More specifically, based on the sensor data and the time information corresponding to the sensor data, the sensor data analysis unit 207 specifies a time at which a predetermined motion pattern occurs in a user or an object on which the sensor device is mounted. Here, the predetermined motion pattern can include, for example, a pattern occurring upon impact of another object on the user or the object on which the sensor device 100 is mounted. For example, when the user is playing a sport and an impact of a ball is generated by the body of the user or a batting tool, such a pattern can occur.

The analysis result processing unit 209 is realized by a processor. The analysis result processing unit 209 supplies the camera control unit 211 and/or the image selection unit 215 with information which is based on the analysis result acquired from the sensor data analysis unit 207. For example, a photographing start/end command based on the analysis result can be output to the camera control unit 211. For example, information which is based on the analysis result and specifies a time serving as an image selection reference can be output to the image selection unit 215.

The camera control unit 211 is realized by a processor. The camera control unit 211 controls the camera 300 based on information acquired from the analysis result processing unit 209 and acquires an image supplied from the camera 300. For example, the camera control unit 211 transmits the photographing start/end command to the camera 300 according to the photographing start/end command acquired from the analysis result processing unit 209. For example, the camera 300 may start/end generation of an image by an imaging element in response to the photographing start/end command. Alternatively, the camera 300 may start/end transmission of the image generated by the imaging element to the smartphone 200 in response to the photographing start/end command. The camera 300 may start/end recording of an image in the camera 300 in response to the photographing start/end command.

The camera control unit 211 transmits a time adjustment command to the camera 300 based on a time acquired from the time information retention unit 227. The time adjustment command is a command used to adjust a time associated with an image by the camera 300 as in the transmission to the sensor device 100. As described above, by generating the time adjustment command to be transmitted to the camera 300 and the time adjustment command to be transmitted to the sensor device 100 based on a common time acquired from the time information retention unit 227, a time associated with the image can match a time associated with the sensor data. The time adjusted according to the time adjustment command can be associated with the image received from the camera 300 by the camera control unit 211. The camera control unit 211 stores the received image and the time associated with the image in the image retention unit 213.

The image retention unit 213 is realized by a memory or a storage. The image retention unit 213 retains the image acquired from the camera 300 by the camera control unit 211 along with the time associated with the image. Here, the image retention unit 213 can function as a buffer that has a predetermined size and continues to retain continuous images cyclically. That is, after the image is supplied from the image retention unit 213 to the image selection unit 215, the image can be destroyed, for example, when its capacity is less than a predetermined threshold value. The images stored in the image retention unit 213 may be treated as still images or moving images and are images continuously photographed at a predetermined interval (or frame rate) in both cases.

The image selection unit 215 is realized by a processor. The image selection unit 215 selects one or more images among the images stored in the image retention unit 213 based on information supplied from the analysis result processing unit 209. More specifically, the image selection unit 215 selects one or more images from a series of images including a user or an object photographed at a predetermined interval according to a time which is specified by the sensor data analysis unit 207 and at which a predetermined motion pattern occurs in the user or the object. In this case, the image selection unit 215 may select the images so that a moving image is configured at a predetermined frame rate or may select each independent image as a still image. A more specific example of the selection of the images by the image selection unit 215 will be described below.

The still image recording unit 217 and the moving image recording unit 219 are realized by processors. The still image recording unit 217 records one or more images selected by the image selection unit 215 as still images. The moving image recording unit 219 records one or more images selected by the image selection unit 215 as a moving image. The still image and the moving image are permanently recorded in the data retention unit 221. The data retention unit 221 is realized by a memory or a storage.

The display control unit 223 is realized by a processor. The display control unit 223 displays the still image or the moving image retained in the data retention unit 221 on the display unit 225. The display unit 225 is realized by a liquid crystal display (LCD), an organic electro-luminescence (EL) display, or the like. For example, the still image or the moving image may be loaded on a play support application supplied in the smartphone 200 to be displayed. For example, the still image may be displayed alone as a digest image, a thumbnail image, or the like or the plurality of still images may be combined and displayed like continuous photos showing a series of actions.

(3. Examples of Image Selection)

In the embodiment, as described above, for example, the time of the sensor data matches the time of the image because the time adjustment command is transmitted based on the time information common to the sensor device 100 and the camera 300. The images can be selected using this in various schemes and, for example, images of a so-called important moment can be extracted and presented to the user. Hereinafter, several examples of selection of the images will be described with reference to FIGS. 3 to 6.

In the embodiment, synchronization based on a time at which sensor data and an image are received in the smartphone 200 is not adopted because a time error would be caused by communication between the sensor device 100 and the smartphone 200 and between the camera 300 and the smartphone 200. The time error caused by the communication can occur, for example, when distances up to the smartphone 200 with the sensor device 100 and the camera 300 are different, communication schemes are different (for example, when one side performs communication with Bluetooth (registered trademark) and the other side performs network communication via a server), or the capacities of transmitted and received data (sensor data and image data) are different.

Accordingly, in another embodiment, for example, when the sensor device and the camera are located at substantially the same distance from the smartphone or the communication schemes are the same and the time error caused due to the communication is allowable, the synchronization based on a time at which sensor data and an image are received may be adopted. Even in this case, image selection to be described below can be performed likewise only with slight deterioration in precision (within the allowable range, as described above).

(3-1. Example in which Single Still Image is Selected)

FIG. 3 is a diagram for describing an example in which a single still image is selected according to the embodiment of the present disclosure. Referring to FIG. 3, in this example, the image selection unit 215 selects a single image as a still image at an impact occurrence time indicated by the sensor data. For example, the impact occurrence time can be specified as a time at which a change in acceleration of a large amplitude with a high frequency occurs in the detection result of an acceleration sensor acquired as the sensor data.

In an example of image selection to be described below, for the purpose of description, numbers of 01 to 18 are given to a series of images received from the camera 300 by the camera control unit 211 and temporarily retained in the image retention unit 213. Images 01 to 18 are photographed at a predetermined time interval (frame rate). The image numbers have no meaning and, for example, images may also be received from the camera 300 before image 01 and after image 18.

In the illustrated example, as the result of the matching between the times of the sensor data and the images, image 14 is specified as an image photographed at the impact occurrence time detected based on the sensor data. Accordingly, the image selection unit 215 selects image 14 as a still image capturing an impact moment. For example, in tennis, there is a high probability of an impact occurrence moment of a ball, such as serve, stroke, or smash, with respect to a racket being an important moment. Accordingly, there is a high probability of image 14 capturing the impact moment being a best shot of the important moment.

Without limitation to the case of tennis, in other ball games, there is also a high probability of an impact of a ball with respect to a batting tool such as a racket or a bat or an impact occurrence moment of a ball with respect to the body of a user being an important moment. In games other than ball games, there is also a high probability of an impact occurring on the body of a user or an instrument with respect to the surface of the earth, a floor, or the like being an important moment. Accordingly, in many cases, as described above, by selecting an image corresponding to a time at which an impact occurs in a user or an object on which a sensor is mounted as a still image, there is a probability of a best shot capturing an important moment being obtained.

(3-2. Example in which Continuous Photos are Selected)

FIG. 4 is a diagram for describing an example in which continuous photos are selected according to the embodiment of the present disclosure. Referring to FIG. 4, in this example, the image selection unit 215 selects a plurality of images photographed in a predetermined section before and after an impact occurrence time detected based on the sensor data, as in the example of FIG. 3, as a series of images forming continuous photos.

In the illustrated example, as the result of the matching between the times of the sensor data and the image, image 14 is specified as an image photographed at the impact occurrence time detected based on the sensor data. The image selection unit 215 selects a plurality of images skipping some images in a predetermined section before and after the impact occurrence time in order to generate continuous photos showing a motion of the user before and after the impact. More specifically, the image selection unit 215 selects images 04, 08, 11, 13, 14, 15, 17, etc. in the illustrated range (continues to select images, although images after image 17 are not illustrated). Here, for example, the predetermined section in which the images are selected may be determined according to a predetermined time, as in an example of a moving image to be described below. Alternatively, the section may be determined according to a predetermined number of the series of images (that is, the number of frames).

Here, the image selection unit 215 does not select the images temporally at an equal interval. More specifically, the image selection unit 215 selects the images such that the skipped interval is lengthened in accordance with temporal separation from the impact moment (image 14). For example, an image selected before the impact moment (image 14) is image 13 located immediately before the impact moment. The skipped interval is gradually expanded toward the past from image 13 in such a manner that one image is skipped and image 11 selected, two images are skipped and image 08 selected, and then three images are skipped and image 04 selected.

For example, when a user hits a ball with a racket, displacement per time increases most in the motions of the user and the racket before and after a ball impact moment, and the displacement per time tends to decrease in accordance with temporal separation from the impact. Accordingly, as described above, the image selection unit 215 can select natural images when viewed as continuous photos by selecting the images at unequal intervals with reference to the impact moment.

As an additional configuration, the image selection unit 215 may allow the numbers of images selected before and after the impact to be different by allowing the lengths of the predetermined section to be different before and after the impact. In the illustrated example, the image selection unit 215 selects one image (image 14) at the impact moment and four images (images 04, 08, 11, and 13) before the impact, whereas the image selection unit 215 may select only three images (images 15, 17, 20 (image 20 is not illustrated)) after the impact. For example, when the user hits the ball with the racket and a motion (take-back) before the impact tends to be focused more than a motion (follow-through) after the impact, the foregoing additional configuration can be effective.

(3-3. Example in which Section of Moving Image is Set)

FIG. 5 is a diagram for describing an example in which a section of a moving image is set according to the embodiment of the present disclosure. Referring to FIG. 5, in this example, the image selection unit 215 selects a plurality of images photographed in a predetermined section before and after an impact occurrence time detected based on the sensor data as a series of frame images forming a moving image, as in the example of FIG. 3.

In the illustrated example, as the result of the matching between the times of the sensor data and the image, image 14 is specified as an image photographed at the impact occurrence time detected based on the sensor data. The image selection unit 215 selects images of the predetermined section including image 14 as the frame images forming a moving image in order to generate a moving image including an impact moment. More specifically, the image selection unit 215 selects the images in a range of a predetermined time t before and after the impact moment as the frame images forming the moving image. Although only the images before the impact moment are illustrated in the drawing, the same also applies to the images after the impact moment. Alternatively, instead of the predetermined time t, a series of a predetermined number of images (that is, the number of frames) may be used.

In the embodiment, as described above, the image retention unit 213 can function as a buffer that has a predetermined size and records a series of images cyclically. The still image recording unit 217 or the moving image recording unit 219 reads the images selected by the image selection unit 215 from the buffer and permanently records the images in a data storage unit, so that the images capturing an important moment can be stored without missing the images while using the buffer with a limited size. This example is advantageous in that the size of the buffer may be smaller than, for example, when images captured during the entire play time are temporarily stored, image analysis or the like is performed later, and a section of an important moment is retrieved and in that a heavy-load process such as long-term image analysis for a moving image may not be performed.

As an additional configuration, the image selection unit 215 may set values of the predetermined time t for determining a section of a moving image to be different before and after the impact moment, as in the additional configuration in the example of FIG. 4.

(3-4. Example in which Continuous Motion Pattern is Detected)

FIG. 6 is a diagram for describing an example in which images are selected based on a continuous motion pattern according to the embodiment of the present disclosure. Referring to FIG. 6, in this example, the image selection unit 215 selects a plurality of images photographed in a section determined based on a start time and/or an end time of a continuous motion pattern detected from the sensor data as a series of frame images forming a moving image.

In the embodiment, a predetermined motion pattern detected by the sensor data analysis unit 207 can include a continuous motion pattern occurring before an impact or occurring after the impact along with or instead of a pattern occurring due to the impact. In the illustrated example, for example, a pattern corresponding to a continuous motion occurring in a user or an object (racket or the like) can be defined in the detection result of an acceleration sensor acquired as the sensor data. The continuous motion is different from a momentary motion such as an impact in that the continuous motion has a temporal length to some extent. The continuous motion can include, for example, a motion occurring in association with an impact of a ball on a racket, such as "take-back" occurring before the impact or "follow-through" occurring after the impact. The motion pattern corresponding to the motion is referred to as a continuous motion pattern in the present specification.

In the illustrated example, a section from a start time of the motion pattern of "take-back" occurring before the impact and detected by the sensor data analysis unit 207 to an end time of the motion pattern of "follow-through" occurring after the impact detected by the sensor data analysis unit 207 is set as a predetermined section, and a series of frame images photographed in this section is selected by the image selection unit 215. In this case, information temporally specifying an impact moment may not necessarily be provided to the image selection unit 215.

The selection of the predetermined section based on the start time or the end time of the continuous motion pattern as in the foregoing example can also be applied to, for example, the selection of the series of images forming the continuous photos as in the example illustrated in FIG. 4. By selecting the images using the continuous motion pattern occurring before and after the impact, the images of a meaningful section associated with the impact can be extracted more accurately than, for example, when the predetermined section is determined based on the predetermined time or the number of frames.

Unlike the momentary motion pattern such as an impact, in the case of the continuous motion pattern, the sensor data analysis unit 207 can determine start of the motion pattern in real time when a motion according to a pattern continues for some time. Therefore, for example, when start of a continuous motion pattern (for example, take-back) occurring before an impact is detected in real time, the camera 300 can be controlled based on information supplied to the camera control unit 211 by the analysis result processing unit 209 such that photographing starts or transmission of photographed images to the smartphone 200 starts.

In the case of the continuous motion pattern, occurrence of a motion can be specified when the motion according to a pattern continues for some time. Accordingly, when the motion according to the pattern ends, the sensor data analysis unit 207 can also determine the end of the motion pattern in real time. Therefore, for example, when the end of the continuous motion pattern (for example, follow-through) occurring after the impact is detected in real time, the analysis result processing unit 209 can also control the camera 300 based on information supplied to the camera control unit 211 by the analysis result processing unit 209 such that the photographing ends or the transmission of the photographed images to the smartphone 200 ends.

In the control of the camera 300 at the time of the end of the motion pattern, the real time is not necessary at the time of the start (slight delay is allowable). Therefore, the same process can also be performed on, for example, a momentary motion pattern due to an impact as well as the continuous motion pattern. That is, when the end of the motion pattern due to the impact is detected, the camera 300 may be controlled such that the photographing ends or the transmission of the photographed images to the smartphone 200 ends. However, a motion (for example, follow-through) subsequent to the impact is also meaningful in many cases. Therefore, in the case of a momentary motion pattern, the camera 300 may be controlled at the time of the end of a motion pattern after the motion pattern ends and then a predetermined time passes.

For example, in the examples illustrated in FIGS. 3 to 5, one or more images are detected based on the time of the impact moment after the impact moment is detected based on the sensor data. Since the process is realized only based on the detection of the impact moment, it is at least necessary for the camera 300 to perform the photographing continuously and to accumulate the series of photographed images in the image retention unit 213 or the camera 300 temporarily. However, for example, when it is necessary to reduce battery consumption of the camera 300 or the smartphone 200, it is not desirable to perform photographing or transmission continuously. As described above, when a motion pattern corresponding to a motion before or after an impact moment can be detected based on the sensor data, the photographing or the transmission can start and end according to the detection of the motion pattern, and thus battery consumption can be reduced. As another example, when the camera 300 can photograph two kinds of images with high resolution and low resolution (for example, the camera 300 may include a plurality of image sensors or image processing on the photographed images may be switched), the images to be supplied to the smartphone 200 may be switched from the images with low resolution to the images with high resolution according to detection of a motion pattern.

A motion pattern may be detected independently from an impact. For example, when a motion pattern can be defined even for a predetermined motion accompanied by an impact in a sport, the image selection unit 215 may retrieve one or more images with reference to a start time and an end time of the motion pattern.

In the above description, the detection result of the acceleration sensor has been exemplified as the example of the sensor data. However, along with or instead of the detection result, a detection result of a gyro sensor or an angular velocity sensor may be used as the sensor data. Further, a geomagnetic sensor, an atmosphere sensor, a sound sensor, an optical sensor, or the like can also be used according to a kind of action (not limited to sports) of the user.

(4. Examples of Applications)

Next, examples of applications according to an embodiment of the present disclosure will be described with reference to FIGS. 7 to 16. For example, screens of the applications to be described below are displayed on the display unit 225 by the display control unit 223 of the smartphone 200.

(4-1. Shot Diagnosis Application)

First, an example of a shot diagnosis application for tennis will be described with reference to FIGS. 7 to 12.

FIG. 7 is a diagram illustrating a start screen of a shot diagnosis application. Referring to FIG. 7, a screen 2000 is displayed on a display of the smartphone 200. The screen 2000 includes a through image 2010, a measurement start button 2020, a sensor waveform 2030, and an information button 2040.

The through image 2010 is an image photographed in real time by the camera 300. In this example, the camera 300 is installed at a predetermined position of a court side and photographs images including a user who is serving. Alternatively, when the camera 300 is built in the smartphone 200, the smartphone 200 may be disposed on a tripod or the like at a predetermined position of a court side. By disposing the camera 300 so that a positional relation between the court and the user becomes a predetermined relation, a shot of the user can be diagnosed based on the images.

The measurement start button 2020 is a button used to start measurement for shot diagnosis. For example, when the measurement start button 2020 is pressed via a touch panel, the smartphone 200 may control the sensor device 100 so that acquisition of the sensor data and transmission of the sensor data to the smartphone 200 start in the sensor device 100. The sensor waveform 2030 is displayed for, for example, a visual effect. When the measurement does not start, a waveform may not be displayed in the sensor waveform 2030. The information button 2040 is a button used to display information regarding a manual, a tutorial, or the like of the shot diagnosis application.

FIG. 8 is a diagram illustrating a screen during measurement in the shot diagnosis application. When the measurement start button 2020 is pressed on the start screen illustrated in FIG. 7, the measurement starts. The screen 2000 during the measurement includes the through image 2010, the sensor waveform 2030, a cancellation button 2050, and a measurement time indication 2060.

As the sensor waveform 2030, a waveform based on the sensor data detected by the sensor of the sensor device 100 may be actually displayed. In the illustrated example, however, when an impact of a ball is detected based on the sensor data, a waveform indicating the impact is displayed as the sensor waveform 2030. That is, the sensor waveform 2030 may be a schematic waveform indicating a change in the sensor data. The user can interrupt the measurement by pressing the cancellation button 2050. The measurement time indication 2060 indicates an elapsed time after the measurement start button 2020 is pressed and the measurement starts.

FIG. 9 is a diagram illustrating a screen during analysis in the shot diagnosis application. When the screen during the measurement illustrated in FIG. 8 is displayed and the user performs a shot (serve), the measurement automatically ends and analysis starts. At this time, in the smartphone 200, occurrence of an impact of a ball due to the shot is detected through the analysis of the sensor data by the sensor data analysis unit 207. For example, the sensor data analysis unit 207 sets an analysis target section with reference to a time at which the impact occurs and extracts various kinds of information regarding the shot, e.g., information regarding a swing speed, a ball speed, ball spin, and the like. Although not illustrated in FIG. 2, the sensor data analysis unit 207 may use not only the sensor data but also images acquired from the camera 300 by the camera control unit 211 for the analysis.

While the sensor data analysis unit 207 performs the analysis, a screen 2100 illustrated in FIG. 9 is displayed. The screen 2100 includes a progress bar 2110, a cancellation button 2120, and a background image 2130. The progress bar 2110 indicates an analysis progress status. The user can interrupt the analysis by pressing the cancellation button 2120. For example, the background image 2130 may be continuous photos before and after a shot to be described below, as illustrated, or may be a single image capturing a shot moment.

FIG. 10 is a diagram illustrating a result screen of the shot diagnosis application. Referring to FIG. 10, a screen 2200 includes a shot image 2210, shot information 2220, a shot position indication 2230, and an all-shots display button 2240.

The shot image 2210 is an image indicating the form of a shot. The shot image 2210 may be a still image or a moving image. The shot image 2210 may include a ball trajectory indication 2250. For example, the ball trajectory indication 2250 continuously expresses a trajectory of a ball at the time of a shot based on images of a predetermined section, selected based on the sensor data by the image selection unit 215, before and after an impact of a ball due to the shot. In the ball trajectory indication 2250, the entire trajectory from the start of the shot to the end of the shot may be simultaneously displayed or the trajectory may be gradually displayed as an animation.

The shot information 2220 includes a swing speed, a ball speed, and ball spin in the illustrated example. For example, the information may be calculated based on the analysis of the images photographed by the camera 300, may be calculated based on the sensor data acquired by the sensor device 100, or may be calculated based on both of the analysis and the sensor data. Items displayed as the shot information 2220 are not limited to the illustrated examples, but other items such as shot power may be displayed.

The shot position indication 2230 displays a position at which an impact of a ball occurs on a racket along with the image of the racket. For example, the impact position can be estimated by identifying a vibration pattern occurring in the racket at the time of the impact based on the sensor data detected by the sensor device 100. The all-shots display button 2240 is a button for transition to a screen on which information regarding all shots including other shots analyzed previously are displayed.

FIG. 11 is a diagram illustrating a continuous photo screen of the shot diagnosis application. Referring to FIG. 11, a screen 2300 includes continuous photos 2310, shot information 2220, a shot position indication 2230, and an all-shots display button 2240. For example, the screen 2300 can be displayed by flicking a result information display portion of the shot information 2220 or the like on the result screen illustrated in FIG. 10 to the left. The display may be returned to the result screen by flicking a result information display portion on the screen 2300 to the right. The shot information 2220, the shot position indication 2230, and the all-shots display button 2240 are the same indications as those on the screen 2200 illustrated in FIG. 10. The continuous photos 2310 will be described below in description of a continuous photo generation application. That is, a continuous photo screen of a shot diagnosis application is a screen in which the result screen illustrated in FIG. 10 is combined with continuous photos to be described below.

FIG. 12 is a diagram illustrating a reproduction control screen of the shot diagnosis application. Referring to FIG. 12, a screen 2400 includes the shot image 2210, the shot information 2220, the shot position indication 2230, the all-shots display button 2240, and reproduction control 2410. For example, the screen 2400 can be displayed by tapping the shot image 2210 on the result screen illustrated in FIG. 10. The display may be returned to the result screen again on the screen 2400 by tapping the shot image 2210. Reproduction of the shot image 2210 can be controlled on the screen 2400 through a manipulation via the reproduction control 2410. For the reproduction control 2410, for example, manipulations such as start, stop, seek, and the like may be performed as in normal reproduction control or some of the manipulations may be restricted. For the reproduction control 2410, for example, only manipulations of pause, restart, frame advance, and jump to the beginning of a moving image of the shot image 2210 may be performed.

In the shot diagnosis application described above, the end of the measurement and the start of the analysis are automatically controlled according to execution of a shot by the user. Accordingly, the user can continue a play as usual after performing a manipulation to start the measurement. Since the images to be used for the analysis are automatically selected based on the sensor data by the image selection unit 215 and, consequently, the analysis target section is restricted to a portion before and after an impact due to a shot, the result of the analysis can be quickly obtained. As another example, the measurement may be automatically started without a manipulation of the user based on a detection result of a motion pattern by the sensor data analysis unit 207.

(4-2. Continuous Photo Generation Application)

Next, an example of a continuous photo generation application will be described with reference to FIGS. 13 to 16.

FIG. 13 is a diagram illustrating a start screen of a continuous photo generation application. Referring to FIG. 13, a screen 2500 includes a through image 2510, a photographing start button 2520, a sensor waveform 2530, and an information button 2540.

The through image 2510 is an image photographed in real time by the camera 300. Unlike the case of the shot diagnosis application, the camera 300 can be installed at any position in this example. When the camera 300 is built in the smartphone 200, the smartphone 200 may be disposed on a tripod or the like at any position of a court side. Alternatively, the camera 300 or the smartphone 200 may be gripped by a user other than the user who is playing tennis.

The photographing start button 2520 is a button used to start photographing. For example, when the photographing start button 2520 is pressed via a touch panel, the smartphone 200 may control the sensor device 100 so that acquisition of the sensor data and transmission of the sensor data to the smartphone 200 starts in the sensor device 100. As will be described below, a plurality of images forming continuous photos are selected based on the sensor data by the image selection unit 215. Therefore, the through image 2510 does not necessarily include continuous photos when the photographing start button 2520 is pressed. As in the case of the shot analysis application, the sensor waveform 2030 is displayed for, for example, a visual effect. The information button 2540 is a button used to display information regarding a manual, a tutorial, or the like of the continuous photo generation application.

FIG. 14 is a diagram illustrating a screen during photographing in the continuous photo generation application. When the photographing start button 2520 is pressed on the start screen illustrated in FIG. 13, a photographing preparation state starts. In the photographing preparation state, when a shot is performed by the user, the sensor device 100 acquires the sensor data and the sensor data is transmitted to the smartphone 200 so that the continuous photos are generated from images before and after the shot. The screen 2500 in the photographing preparation state includes the through image 2510, the sensor waveform 2530, a cancellation button 2550, and a photographing time indication 2560. The user can interrupt the photographing by pressing the cancellation button 2550. The photographing time indication 2560 indicates an elapsed time after the photographing start button 2520 is pressed.

FIG. 15 is a diagram illustrating a screen during generation in the continuous photo generation application. Referring to FIG. 15, a screen 2600 includes a progress bar 2610. When the screen during the photographing illustrated in FIG. 14 is displayed and the user performs a shot (serve), the photographing automatically ends and generation of the continuous photos starts. At this time, in the smartphone 200, occurrence of an impact of a ball due to the shot is detected through the analysis of the sensor data by the sensor data analysis unit 207. The image selection unit 215 sets a section of the continuous photos with reference to a time at which the impact occurs and selects a plurality of images in the section to generate the continuous photos. As described above, the time interval of the images selected to generate the continuous photos may not be uniform. The sensor data analysis unit 207 may detect a motion pattern accompanying the impact before and after through the analysis of the sensor data and the image selection unit 215 may set the section of the continuous photos according to a start or end time of the motion pattern.

FIG. 16 is a diagram illustrating a generation result screen of the continuous photo generation application. Referring to FIG. 16, a screen 2700 includes continuous photos 2710.

The continuous photos 2710 are generated by cutting regions of the user who is playing with the same size from the plurality of images selected through the above-described process by the image selection unit 215 and arranging the cut images. In the illustrated example, the continuous photos chronologically proceeding from the left to the right are exemplified, but the examples of the continuous photos are not limited thereto. For example, the photos may be arranged vertically at two or more stages or the number of photos arranged horizontally may be larger or smaller than the number of photos illustrated in the example.

In the above-described continuous photo generation application, the end of the photographing and the start of the generation of the continuous photos are automatically controlled according to execution of a shot by the user. Accordingly, the user can continue the play as usual after performing a manipulation to start the photographing. The images forming the continuous photos are automatically selected based on the sensor data by the image selection unit 215 and, consequently, the continuous photos capturing portions before and after the shot can be quickly generated.

(5. Hardware Configuration)

Next, a hardware configuration of an information processing device according to an embodiment of the present disclosure will be described with reference to FIG. 17. FIG. 17 is a block diagram illustrating an example of the hardware configuration of the information processing device according to the embodiment of the present disclosure. For example, the smartphone, the camera, and the server according to the foregoing embodiment can be realized through an illustrated information processing device 900.

The information processing device 900 includes a central processing unit (CPU) 901, a read-only memory (ROM) 903, and a random access memory (RAM) 905. Also, the information processing device 900 may include a host bus 907, a bridge 909, an external bus 911, an interface 913, an input device 915, an output device 917, a storage device 919, a drive 921, a connection port 923, and a communication device 925. The information processing device 900 may further include an imaging device 933 and a sensor 935 as necessary. The information processing device 900 may include a processing circuit called a digital signal processor (DSP) or an application specific integrated circuit (ASIC), instead of or in addition to the CPU 901.

The CPU 901 functions as an arithmetic processing device and a control device and controls all or some of the operations in the information processing device 900 according to various programs recorded in the ROM 903, the RAM 905, the storage device 919, or a removable recording medium 927. The ROM 903 stores a program, an arithmetic parameter, and the like used by the CPU 901. The RAM 905 primarily stores a program used in execution of the CPU 901 and a parameter or the like appropriately changed in execution of the program. The CPU 901, the ROM 903, and the RAM 905 are connected to each other by the host bus 907 including an internal bus such as a CPU bus. Further, the host bus 907 is connected to the external bus 911 such as a Peripheral Component Interconnect/interface (PCI) bus via the bridge 909.

The input device 915 is, for example, an operation unit manipulated by a user, such as a mouse, a keyboard, a touch panel, a button, a switch, and a lever. Also, the input device 915 may be, for example, a remote control device using an infrared ray or other radio waves or may be, for example, an external connection device 929 such as a mobile phone corresponding to a manipulation of the information processing device 900. Also, the input device 915 includes, for example, an input control circuit that generates an input signal based on information input by a user and outputs the signal to the CPU 901. The user inputs various kinds of data to the information processing device 900 or instructs the information processing device 900 to perform a processing operation by manipulating the input device 915.

The output device 917 includes a device capable of visually or audibly notifying a user of the acquired information. Examples of the output device 917 include display devices such as a liquid crystal display (LCD), a plasma display panel (PDP), and an organic electro-luminescence (EL) display, audio output devices such as a speaker and a headphone, and printer devices. The output device 917 outputs a result obtained through the process of the information processing device 900 as a picture such as text or an image or outputs the result as an audio such as a voice or an acoustic sound.

The storage device 919 is a data storage device configured as an example of the storage unit of the information processing device 900. The storage device 919 includes, for example, a magnetic storage device such as a hard disk device (HDD), a semiconductor storage device, an optical storage device, or a magneto-optical storage device. The storage device 919 stores a program or various kinds of data executed by the CPU 901 and various kinds of data acquired from the outside.

The drive 921 is a reader/writer for the removable recording medium 927 such as a magnetic disk, an optical disc, a magneto-optical disc, or a semiconductor memory, and is built in the information processing device 900 or is attached on the outside thereof. The drive 921 reads information recorded on the mounted removable recording medium 927 and outputs the information to the RAM 905. Also, the drive 921 writes a record on the mounted removable recording medium 927.

The connection port 923 is a port configured to directly connect a device to the information processing device 900. Examples of the connection port 923 include a Universal Serial Bus (USB) port, an IEEE1394 port, and a Small Computer System Interface (SCSI) port. Other examples of the connection port 923 include an RS-232C port, an optical audio terminal, and a High-Definition Multimedia Interface (HDMI) (registered trademark) port. When the external connection device 929 is connected to the connection port 923, various kinds of data can be exchanged between the information processing device 900 and the external connection device 929.

The communication device 925 is, for example, a communication interface including a communication device connected to a communication network 931. Examples of the communication device 925 include communication cards for a wired or wireless Local Area Network (LAN), Bluetooth (registered trademark), and a Wireless USB (WUSB). Also, the communication device 925 may be a router for optical communication, a router for an Asymmetric Digital Subscriber Line (ADSL), or modems for various kinds of communication. For example, the communication device 925 transmits and receives a signal or the like to and from the Internet or another communication device in conformity with a predetermined protocol such as TCP/IP. Also, the communication network 931 connected to the communication device 925 includes networks connected in a wired or wireless manner and includes, for example, the Internet, a household LAN, infrared ray communication, radio-wave communication, or satellite communication.

Examples of the imaging device 933 include an image sensor such as a charge coupled device (CCD) or a complementary metal oxide semiconductor (CMOS) and a device that images an actual space using various members such as lenses controlling formation of an image of a subject in the image sensor and generates a captured image. The imaging device 933 may be a device that captures a still image or may be a device that captures a moving image.

Examples of the sensor 935 include various sensors such as an acceleration sensor, a gyro sensor, a geomagnetic sensor, an optical sensor, or an audio sensor. The sensor 935 acquires, for example, information regarding a posture state of the information processing device 900, such as a posture of the casing of the information processing device 900 or information regarding a surrounding environment of the information processing device 900, such as brightness or noise of the surroundings of the information processing device 900. Also, the sensor 935 may include a Global Positioning System (GPS) sensor that receives GPS signals and measures the latitude, longitude, and altitude of the device.

The example of the hardware configuration of the information processing device 900 has been described above. Each of the foregoing constituent elements may be configured using a general-purpose member or may be configured by hardware specialized for the function of each constituent element. The configuration can be modified appropriately according to a technical level at the time of realizing the embodiments.

(6. Supplement)

The embodiments of the present technology can include, for example, the above-described information processing device (a smartphone, a camera, a server, or the like), a system, an information processing device, an information processing method performed by the information processing device or the system, a program causing the information processing device to function, and a non-transitory type medium having the program stored therein.

The preferred embodiments of the present disclosure have been described in detail with reference to the appended drawings, but the technical scope of the present disclosure is not limited to the examples. It should be understood by those skilled in the art that various modifications, combinations, sub-combinations and alterations may occur depending on design requirements and other factors insofar as they are within the scope of the appended claims or the equivalents thereof.

The advantageous effects described in the present specification are merely descriptive and exemplary, and thus are not restrictive. That is, according to an embodiment of the technology related to the present disclosure, it is possible to obtain other advantageous effects apparent to those skilled in the art along with the foregoing advantageous effects or instead of the foregoing advantageous effects from the description of the present specification.

(1) According to a non-transitory computer readable storage device embodiment, a storage medium has an application stored therein. The application has instructions that when executed by processing circuitry configure the processing circuitry to receive sensor data from a sensor, the sensor being attached to a person or attached to an item used by the person; and analyze a motion pattern in the sensor data to identify a predetermined event in the motion pattern, the predetermined event captured in an image or series of images by an image capture device.

(2) The non-transitory computer readable storage device of (1), wherein the instructions further configure the processing circuitry to generate a control signal to control an image capture process in the image capture device to select the image or series of images, wherein the item is an object.

(3) The non-transitory computer readable storage device of (2), wherein the control signal includes an image capture start command and/or an end command based on an analysis result of the motion pattern.

(4) The non-transitory computer readable storage device of (2), wherein the instructions further configure the processing circuitry to generate the control signal with information that specifies a time that serves as an image selection reference.

(5) The non-transitory computer readable storage device of (4), wherein the instructions further configure the processing circuitry to generate the control signal with a time adjust command to adjust a time associated with the sensor data to match an image capture time.

(6) The non-transitory computer readable storage device of (1), wherein the instructions further configure the processing circuitry to receive images from the image capture device, wherein the item is an object.

(7) The non-transitory computer readable storage device of (6), wherein the instructions further configure the processing circuitry to learn the motion pattern from the images received from the image capture device.

(8) The non-transitory computer readable storage device of (4), wherein the time corresponds with a predetermined event in the motion pattern.

(9) The non-transitory computer readable storage device of (8), wherein the predetermined event corresponds to an impact on an object by the person or the item used by the person.

(10) The non-transitory computer readable storage device of (2), wherein the instructions further configure the processing circuitry to transmit the control signal to another device, and receive the sensor data from the another device, the another device being a smartphone or wearable computer.

(11) The non-transitory computer readable storage device of (10), wherein the image capture device is a different device than the another device.

(12) The non-transitory computer readable storage device of (11), wherein image capture device uploads images directly to the processing circuitry and the another device relays the sensor data to the processing circuitry.

(13) The non-transitory computer readable storage device of (1) wherein the application is a downloaded application, and the item is an object.

(14) The non-transitory computer readable storage device of (2) wherein the instructions further configure the processing circuitry to synchronize the sensor data with the image or series of images captured by the image capture device.

(15) The non-transitory computer readable storage device of (1), wherein the instructions further configure the processing circuitry to detect an impact occurrence as the predetermined event and select a portion of a series of consecutive images captured before and after the impact occurrence.

(16) The non-transitory computer readable storage device of (15), wherein the instructions further configure the processing circuitry to select the portion of the series of consecutive images by skipping some images in a predetermined section of the series of consecutive images before and after the impact occurrence.

(17) The non-transitory computer readable storage device of (16), wherein an image skipping interval increases as a temporal separation increases relative to the impact occurrence.

(18) An information processing system comprising:

circuitry, the circuitry configured by computer readable instructions to receive sensor data collected by a sensor attached to a person or attached to an item used by the person; and analyze a motion pattern in the sensor data to identify a predetermined event in the motion pattern, the predetermined event captured in an image or series of images by an image capture device.

(19) The system of (18), wherein the circuitry includes a first part disposed in a first device that analyzes the motion pattern, and a second part that is disposed in a second device that sends the sensor data to the first device, and the first device and the second device being separate devices, wherein the item is an object.

(20) The system of (19), wherein the first device is included in one of a smartphone and a wearable computer.

REFERENCE SIGNS LIST 10 system
100 sensor device
200 smartphone
201 transmission unit
203 reception unit
205 sensor device control unit
207 sensor data analysis unit
209 analysis result processing unit
211 camera control unit
213 image retention unit
215 image selection unit
217 still image recording unit
219 moving image recording unit
221 data retention unit
223 display control unit
225 display unit
227 time information retention unit
300 camera
400 server

The invention claimed is:

1. A non-transitory computer readable storage device having computer-readable instructions of an application thereon which when executed by processing circuitry cause the processing circuitry to perform a method comprising:
    receiving sensor data from a sensor, the sensor being attached to a person or attached to an item used by the person;
    analyzing a motion pattern in the sensor data to identify a predetermined event in the motion pattern, the predetermined event being captured in an image or series of images by an image capture device;
    generating a control signal to control an image capture process in the image capture device to select the image or series of images;
    generating the control signal with information that specifies a time that serves as an image selection reference; and
    selecting a portion of a series of consecutive images captured before and after the predetermined event by skipping, at unequal intervals with reference to the predetermined event, some images of the series of consecutive images before and after the predetermined event.

2. The non-transitory computer readable storage device of claim 1,
    wherein the item is an object.

3. The non-transitory computer readable storage device of claim 2, wherein the control signal includes an image capture start command and/or end command based on an analysis result of the motion pattern.

4. The non-transitory computer readable storage device of claim 2, wherein the method further comprises: transmitting the control signal to another device, and
    receiving the sensor data from the another device, the another device being a smartphone or wearable computer.

5. The non-transitory computer readable storage device of claim 4, wherein the image capture device is a different device than the another device.

6. The non-transitory computer readable storage device of claim 5, wherein image capture device uploads images directly to the processing circuitry and the another device relays the sensor data to the processing circuitry.

7. The non-transitory computer readable storage device of claim 2, wherein the method further comprises:
    synchronizing the sensor data with the image or series of images captured by the image capture device.

8. The non-transitory computer readable storage device of claim 1, wherein the method further comprises:
    generating the control signal with a time adjust command to adjust a time associated with the sensor data to match an image capture time.

9. The non-transitory computer readable storage device of claim 1, wherein the method further comprises:
    receiving images from the image capture device,
    wherein the item is an object.

10. The non-transitory computer readable storage device of claim 9, wherein the method further comprises:
    learning the motion pattern from the images received from the image capture device.

11. The non-transitory computer readable storage device of claim 1, wherein the time corresponds with a predetermined event in the motion pattern.

12. The non-transitory computer readable storage device of claim 11, wherein the predetermined event corresponds to an impact on an object by the person or the item used by the person.

13. The non-transitory computer readable storage device of claim 1, wherein the application is a downloaded application, and the item is an object.

14. The non-transitory computer readable storage device of claim 1, wherein the method further comprises:
    detecting an impact occurrence as the predetermined event,
    wherein the item is an object.

15. The non-transitory computer readable storage device of claim 14, wherein an image skipping interval increases as a temporal separation increases relative to the impact occurrence.

16. An information processing system comprising:
    processing circuitry configured to
        receive sensor data collected by a sensor attached to a person or attached to an item used by the person,
        analyze a motion pattern in the sensor data to identify a predetermined event in the motion pattern, the predetermined event being captured in an image or series of images by an image capture device,
        generate a control signal to control an image capture process in the image capture device to select the image or series of images,
        generate the control signal with information that specifies a time that serves as an image selection reference, and
        select a portion of a series of consecutive images captured before and after the predetermined event by skipping, at unequal intervals with reference to the predetermined event, some images of the series of consecutive images before and after the predetermined event.

17. The system of claim 16, wherein the processing circuitry is included in one of a smartphone and a wearable computer.

18. A method comprising:
receiving sensor data from a sensor, the sensor being attached to a person or attached to an item used by the person;
analyzing, via processing circuitry, a motion pattern in the sensor data to identify a predetermined event in the motion pattern, the predetermined event being captured in an image or series of images by an image capture device;
generating, via the processing circuitry, a control signal to control an image capture process in the image capture device to select the image or series of images;
generating, via the processing circuitry, the control signal with information that specifies a time that serves as an image selection reference; and
selecting a portion of a series of consecutive images captured before and after the predetermined event by skipping, at unequal intervals with reference to the predetermined event, some images of the series of consecutive images before and after the predetermined event.

19. The method of claim 18, wherein
the predetermined event corresponds to an impact of a ball with the item used by the person,
the predetermined event is associated with one image, and
the selecting does not skip images immediately before and immediately after the one image associated with the predetermined event, which corresponds to the impact of the ball with the item used by the person.

* * * * *